(12) United States Patent
Olwill et al.

(10) Patent No.: US 9,321,838 B2
(45) Date of Patent: Apr. 26, 2016

(54) THERAPY TARGETING CATHEPSIN S

(75) Inventors: Shane Olwill, Belfast (GB); Christopher Scott, Belfast (GB); Julie Gormley, Belfast (GB); Jaquin Thomas, Belfast (GB); Roberta Burden, Belfast (GB); Darragh McMeel, Belfast (GB); James Johnston, Belfast (GB)

(73) Assignee: Fusion Antibodies Limited (GB)

( * ) Notice: Subject to any disclaimer, the term of this patent is extended or adjusted under 35 U.S.C. 154(b) by 90 days.

(21) Appl. No.: 12/296,704

(22) PCT Filed: Apr. 10, 2007

(86) PCT No.: PCT/GB2007/001312
§ 371 (c)(1),
(2), (4) Date: Apr. 21, 2009

(87) PCT Pub. No.: WO2007/128987
PCT Pub. Date: Nov. 15, 2007

(65) Prior Publication Data
US 2009/0269360 A1    Oct. 29, 2009

(30) Foreign Application Priority Data

Apr. 10, 2006  (GB) .................................. 0607158.3
Oct. 12, 2006  (GB) .................................. 0620255.0

(51) Int. Cl.
| | | |
|---|---|---|
| *C07K 16/00* | (2006.01) | |
| *C07K 16/28* | (2006.01) | |
| *A61K 31/00* | (2006.01) | |
| *A61K 39/395* | (2006.01) | |
| *C07K 16/40* | (2006.01) | |
| *G01N 33/574* | (2006.01) | |
| *A61K 39/00* | (2006.01) | |

(52) U.S. Cl.
CPC .................. *C07K 16/28* (2013.01); *A61K 31/00* (2013.01); *A61K 39/3955* (2013.01); *A61K 39/39558* (2013.01); *C07K 16/40* (2013.01); *G01N 33/57492* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 3,773,919 A | | 11/1973 | Boswell et al. |
| 4,816,567 A | | 3/1989 | Cabilly et al. |
| 4,853,219 A | * | 8/1989 | Alderman et al. ......... 424/139.1 |
| 4,892,538 A | | 1/1990 | Aebischer et al. |
| 5,057,313 A | | 10/1991 | Shih et al. |
| 5,283,187 A | | 2/1994 | Aebischer et al. |
| 6,291,504 B1 | * | 9/2001 | Nugiel et al. ................. 514/403 |
| 6,608,030 B1 | * | 8/2003 | Ploegh et al. ................... 514/13 |
| 2005/0186208 A1 | * | 8/2005 | Fyfe et al. ................... 424/145.1 |

FOREIGN PATENT DOCUMENTS

| | | |
|---|---|---|
| EP | 0 404 097 | 12/1990 |
| WO | 93/11161 | 6/1993 |
| WO | 93/25673 | 12/1993 |
| WO | 03/020287 A2 | 3/2003 |
| WO | 2006/109045 | 10/2006 |

OTHER PUBLICATIONS

Wang et al, J Biol Chem. 2006, 281:6020-9.*
Sekirnik et al, British J of Cancer, 85:1193-1200, 2001.*
Meighan et al, Bioche Soc Trans 26:S47, 1998.*
Burden et al, Clin Cancer Res 15:6042, 2009.*
Ward and Olwill, Plos One 5:e12543, 2010, abstract.*
Joyce, Johanna A. et al.: "Cathepsin cysteine proteases are effectors of invasive growth and angiogenesis during multistage tumorigenesis" Cancer Cell, XX, US, vol. 5, No. 5, May 2004, pp. 443-453.
Kos, J. et al.: "Cathepsin S in tumours, regional lymph nodes and sera of patients with lung cancer: relation to prognosis." British Journal of Cancer, Oct. 19, 2001 5, No. 8, pp. 1193-1200.
Berdowska, I.: "Cysteine proteases as disease markers" Clinica Chimica Acta, Amsterdam, NL, vol. 342, No. 1-2, Apr. 2004, pp. 41-69.
Falgueyret, J-P. et al.: "An activity-based probe for the determination of cysteine cathepsin protease activities in whole cells" Analytical Biochemistry, Academic Press, New York, NY, US, vol. 335, No. 2, Dec. 15, 2004, pp. 218-227.
Shi, G.-P., et al., "Deficiency of the Cysteine Protease Cathespin S Impairs Microvessel Growth," *Circ. Res.*, 2003, vol. 92, pp. 493-500 (printout: pp. 2-9).

* cited by examiner

*Primary Examiner* — Lei Yao
(74) *Attorney, Agent, or Firm* — DLA Piper LLP (US)

(57) ABSTRACT

The invention relates to a method of inhibiting chemotherapy induced upregulation of Cathepsin S on the surface of tumor cells, the method comprising the administration of a Cathepsin S inhibitor to said cells. Also provided is a therapy comprising an anti Cathepsin S antibody, in particular an anti-Cathepsin S antibody which does not inhibit the proteolytic effect of Cathepsin S but nevertheless inhibits angiogenesis and a combination treatment comprising a Cathepsin S inhibitor and a therapeutic agent.

5 Claims, 23 Drawing Sheets

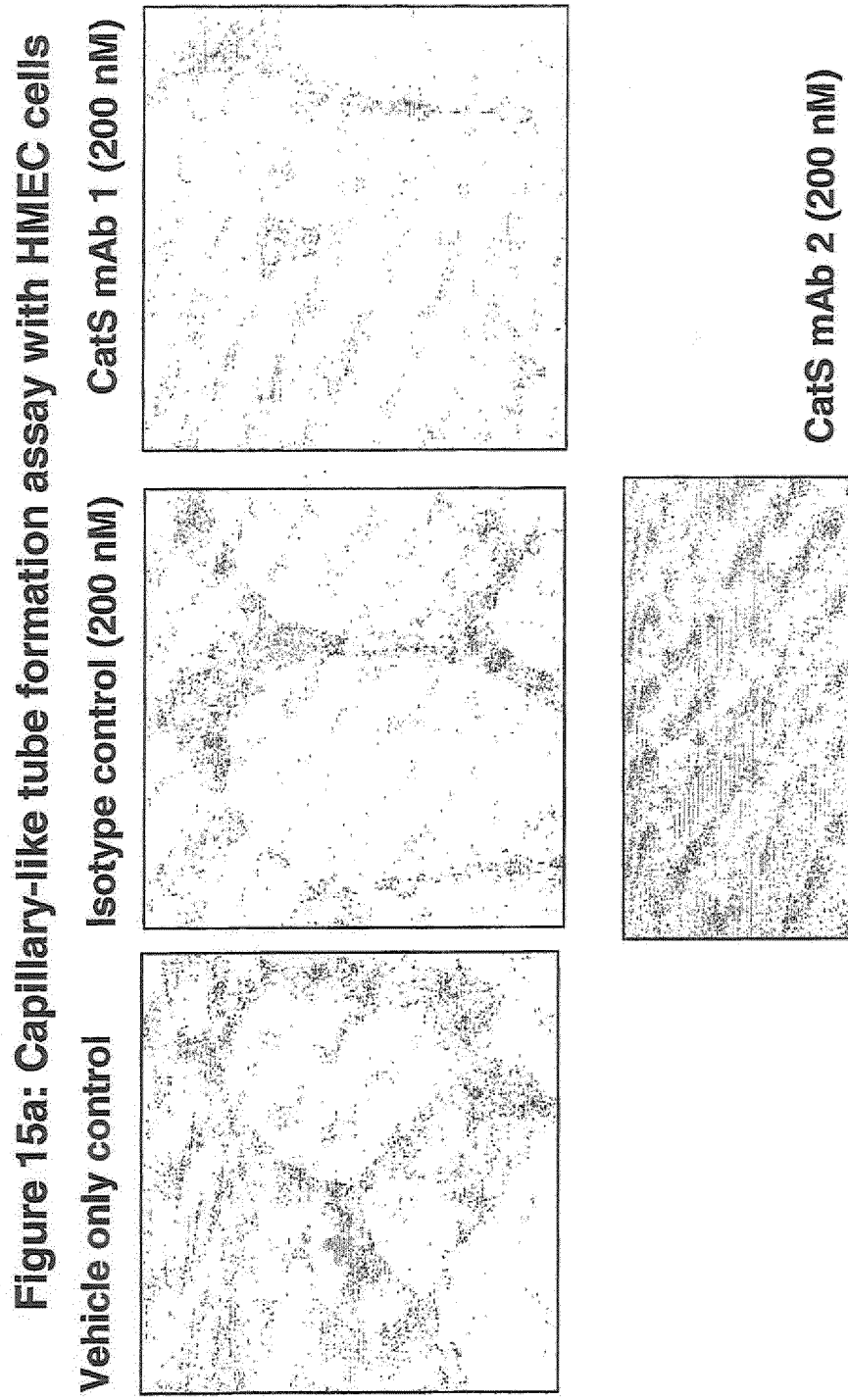

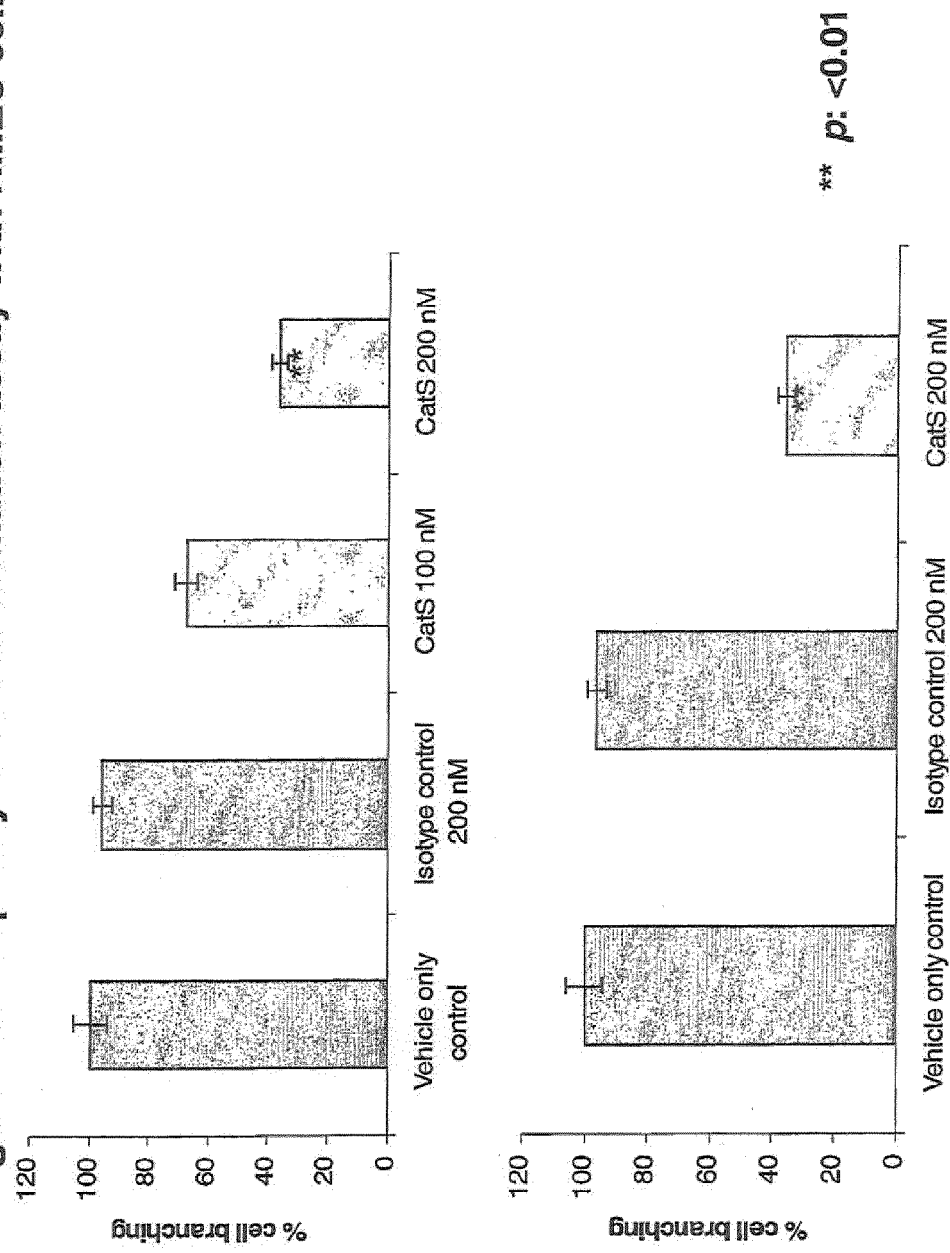

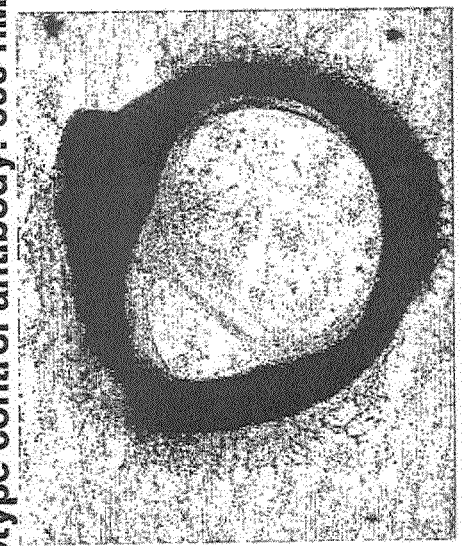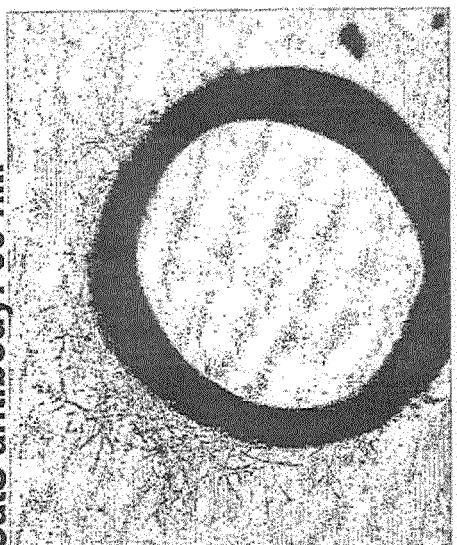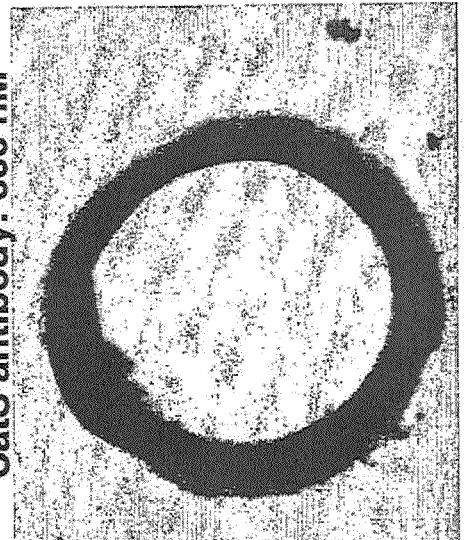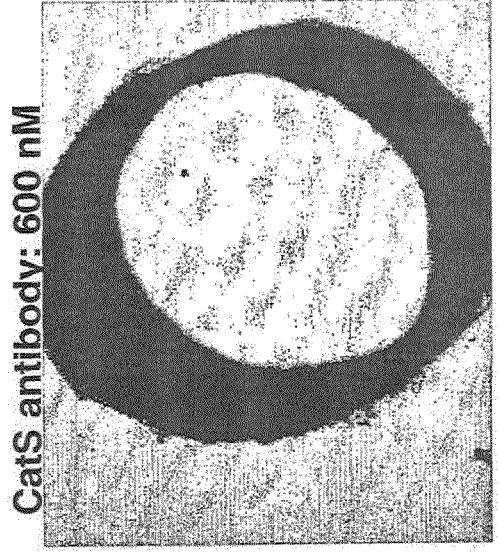
Figure 16a: Rat aorta model

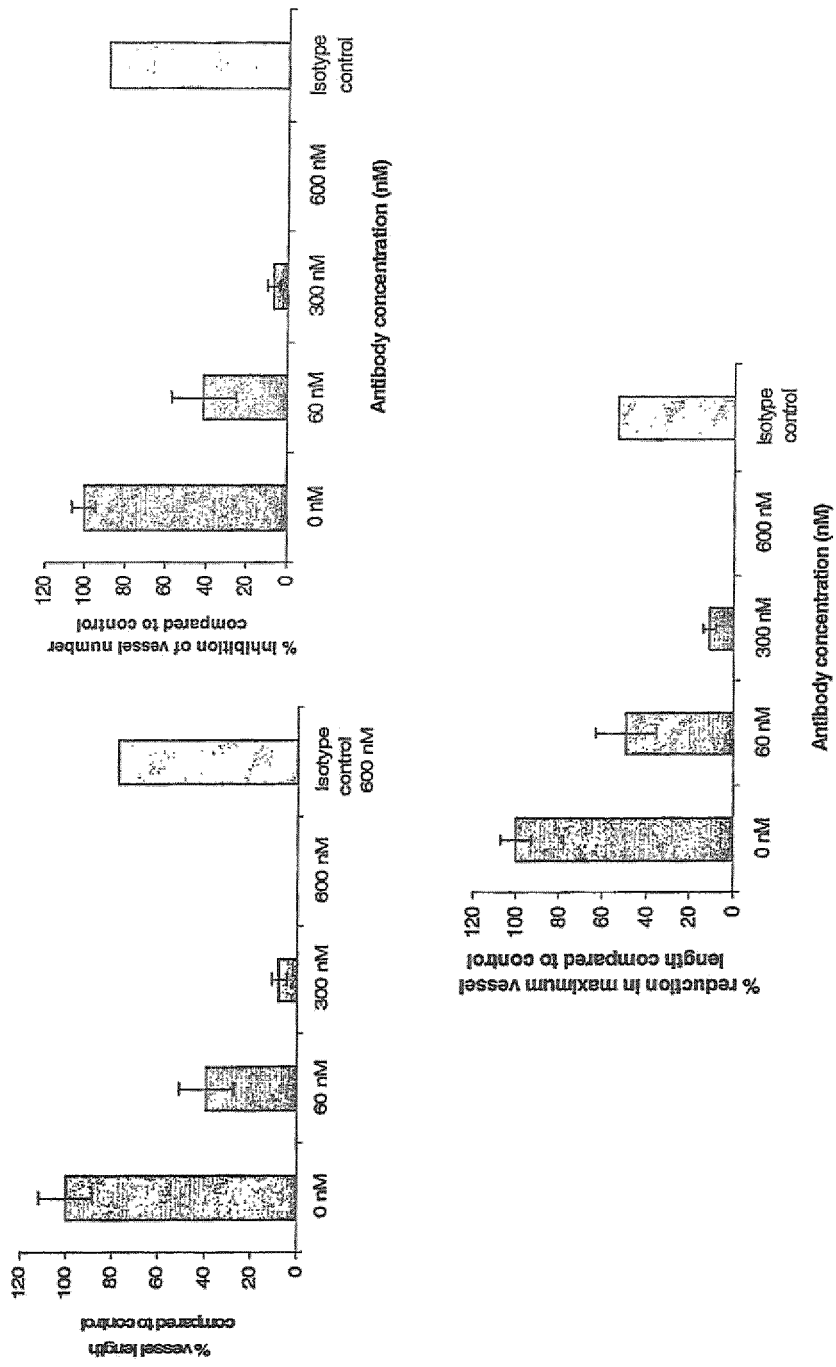
Figure 16b: Rat aorta model

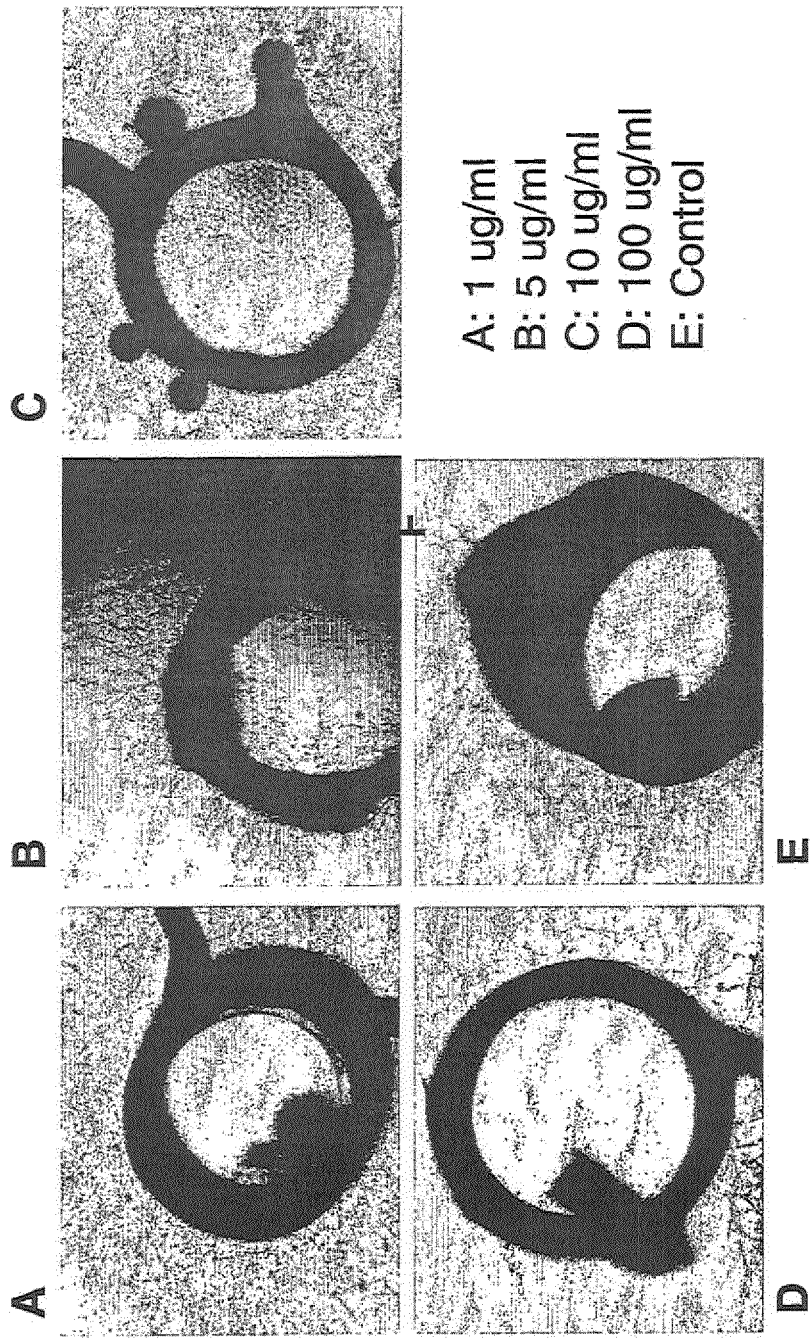
Figure 17a(1): Effect of CatS mAb on the ex-vivo rat aortic ring model of angiogenesis (x4 mag)
A: 1 ug/ml
B: 5 ug/ml
C: 10 ug/ml
D: 100 ug/ml
E: Control

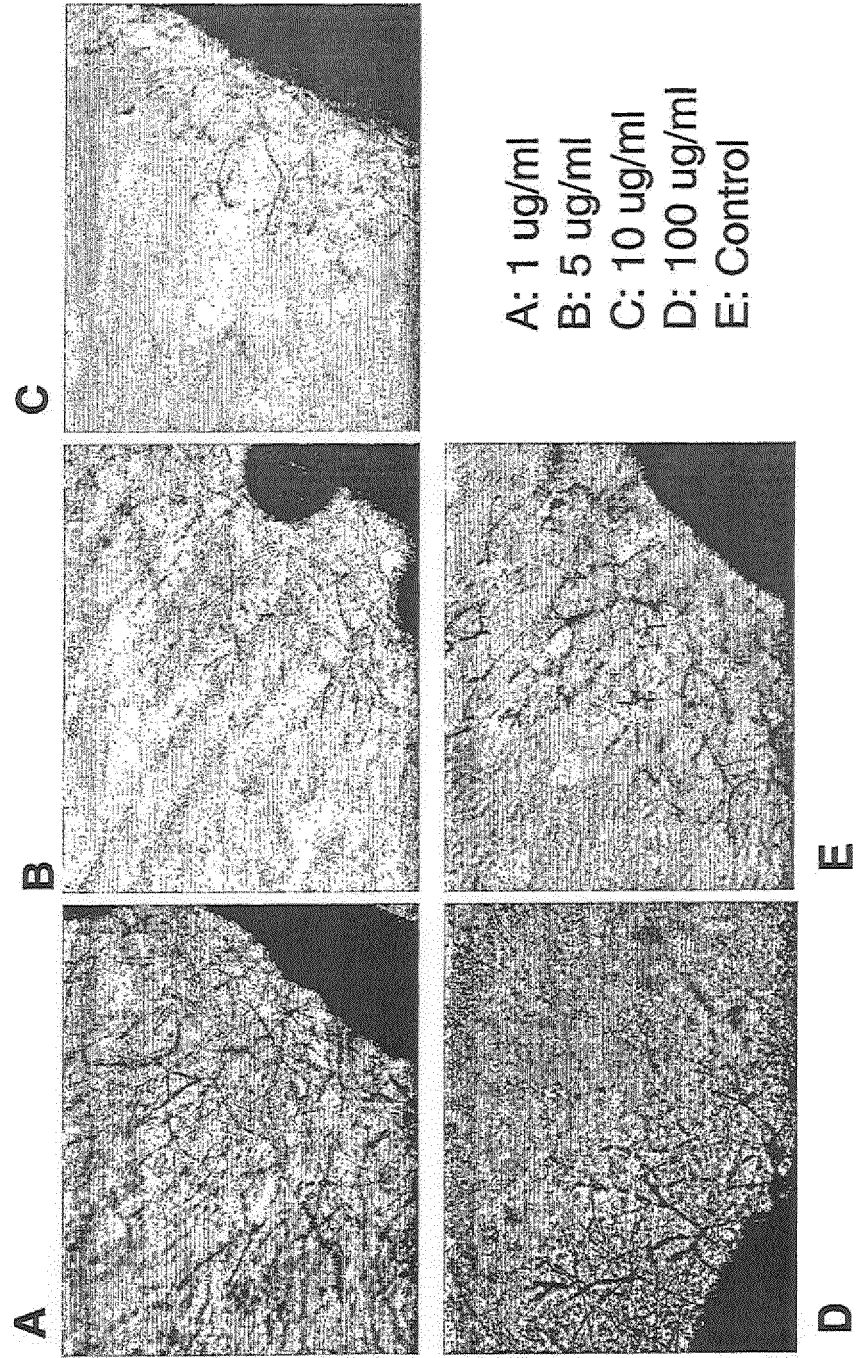
Figure 17a (2): Effect of CatS mAb on the ex-vivo rat aortic ring model of angiogenesis (X20 mag)
A: 1 ug/ml
B: 5 ug/ml
C: 10 ug/ml
D: 100 ug/ml
E: Control

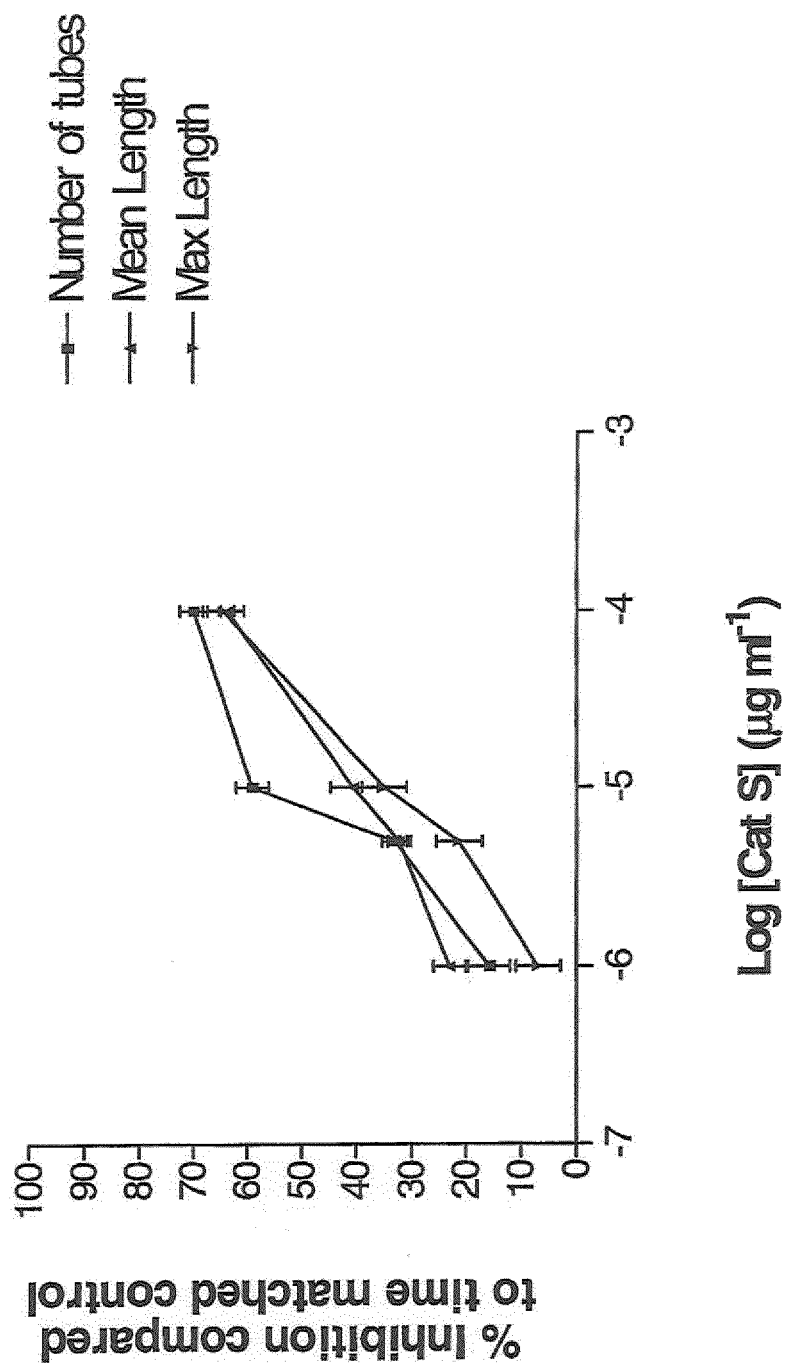
Figure 17b: Effect of CatS mAb on the ex-vivo rat aortic ring model of angiogenesis Consensus Protein Sequence for VH    (SEQ ID NO: 7)

VQLQESGGVLVKPGGSLKLSCAASGFAFSSYDMSWVRQTPEKRLEWVA
YITTGGVNTYYPDTVKGRFTISRDNAKNTLYLQMSSLKSEDTAMYYCARHSYFDYW
GQGTTVTVSS

Consensus Protein Sequence for VL    (SEQ ID NO: 8)

DVLMTQTPLSLPVSLGDQASISCRSSQSLVHSNGNTYLHWYLQKPGQSPKLLI
YKVSNRFSGVPDRFSGSGSGTDFTLKISRVEAEDLGVYFCSQTTHVPPTFGSG
TKLEIKR

Figure 18

THERAPY TARGETING CATHEPSIN S

FIELD OF THE INVENTION

This application relates to methods of treatment of neoplastic disease and compositions for use in such treatments. In particular, it relates to antibody based therapies for the treatment of cancer as well as combination therapies to counteract tumour cell defence mechanisms to chemotherapeutic treatments.

BACKGROUND TO THE INVENTION

Proteases are a large group of proteins that comprise approximately 2% of all gene products (Rawlings and Barrett, 1999). Proteases catalyse the hydrolysis of peptide bonds and are vital for the proper functioning of all cells and organisms. Proteolytic processing events are important in a wide range of cellular processes including bone formation, wound healing, angiogenesis and apoptosis.

The lysosomal cysteine proteases were initially thought to be enzymes that were responsible for non-selective degradation of proteins in the lysosomes. They are now known to be accountable for a number of important cellular processes, having roles in apoptosis, antigen presentation, coagulation, digestion, pro-hormone processing and extracellular matrix remodelling (Chapman et al, 1997).

Cathepsin S (Cat S) is a member of the papain superfamily of lysosomal cysteine proteases. To date, eleven human cathepsins have been identified, but the specific in vivo roles of each are still to be determined (Katunuma et al, 2003). Cathepsins B, L, H, F, O, X and C are expressed in most cells, suggesting a possible role in regulating protein turnover, whereas Cathepsins S, K, W and V are restricted to particular cells and tissues, indicating that they may have more specific roles (Kos et al, 2001; Berdowska, 2004, *Clinica Chimica Acta*. 2004; 342: 41-69).

Cat S was originally identified from bovine lymph nodes and spleen and the human form cloned from a human macrophage cDNA library (Shi et al, *J Biol. Chem.* 1992; 267: 7258-7262). The gene encoding Cat S is located on human chromosome 1q21. The 996 base pair transcript encoded by the Cat S gene is initially translated into an unprocessed precursor protein with a molecular weight of 37.5 kDa. The unprocessed protein is composed of 331 amino acids; a 15 amino acid signal peptide, a 99 amino acid pro-peptide sequence and a 217 amino acid peptide. Cat S is initially expressed with a signal peptide that is removed after it enters the lumen of the endoplasmic reticulum. The propeptide sequence binds to the active site of the protease, rendering it inactive until it has been transported to the acidic endosomal compartments, after which the propeptide sequence is removed and the protease is activated (Baker et al, 2003 Protein Expr Purif. 28, 93-101).

Cat S has been identified as a key enzyme in major histocompatibility complex class II (MHC-II) mediated antigen presentation, by cleavage of the invariant chain, prior to antigen loading. Studies have shown that mice deficient in Cat S have an impaired ability to present exogenous proteins by APCs (Nakagawa et al, *Immunity*. 1999; 10: 207-217). The specificity of Cat S in the processing of the invariant chain Ii, allows for Cat S specific therapeutic targets in the treatment of conditions such as asthma and autoimmune disorders (Chapman et al, 1997).

Pathological Association of Cat S

Alterations in protease control frequently underlie many human pathological processes. The deregulated expression and activity of the lysosomal cysteine protease Cathepsin S has been linked to a range of conditions including neurodegenerative disorders, autoimmune diseases and certain malignancies.

Cat S upregulation has been linked to several neurodegenerative disorders. It is believed to have a role in the production of the β peptide (Aβ) from the amyloid precursor protein (APP) (Munger et al, *Biochem. J.* 1995; 311: 299-305) and its expression has been shown to be upregulated in both Alzheimer's Disease and Down's Syndrome (Lemere et al, 1995). Cat S may also have a role in Multiple Sclerosis through the ability of Cat S to degrade myelin basic protein, a potential autoantigen implicated in the pathogenesis of MS (Beck et al, 2001, *Eur. J. Immunol.* 2001; 31: 3726-3736) and in Creutzfeldt-Jakob disease (CJD) patients, Cat S expression has been shown to increase more than four fold (Baker et al, 2002).

Cathepsin S has been reported to be overexpressed in atherosclerotic and restenosis after angioplasty (Cheng et al, Am. J Pathology, 2006, 168: 685-694). In these conditions, the CatS was reported to co-localise with integrin αvβ3 as a receptor on the vascular smooth muscle cell surface.

Angiogenesis, the development of microvasculature, is an integral process within many normal physiological processes such as normal development and wound healing. Angiogenesis is characterised by the stimulation of endothelial cells to form primary blood vessels where a non-clarified complex interplay exists between the endothelial cells, surrounding microenvironment and a range of pro- and anti-angiogenic factors. However, uncontrolled or inappropriate angiogenesis is accepted as an underlying factor to the pathology of a wide range of diseases including tumour progression and ocular disease.

The association of CatS with angiogenesis was first shown in vitro using CatS deficient endothelial cells (Shi et al, 2003). Microvascular endothelial cells (ECs) have been shown to secrete proteases, permitting penetration of the vascular basement membrane as well as the interstitial extracellular matrix. Treatment of cultured ECs with inflammatory cytokines or angiogenic factors stimulated expression of CatS, and its inhibition reduced microtubule formation. CatS−/− mice displayed defective microvessel development during wound repair in comparison to wild-type controls (Shi et al, 2003).

Further examination of the role of CatS in angiogenesis and tumour growth was demonstrated in a transgenic mouse model for pancreatic islet cell carcinoma. CatS−/− mice were found to develop significantly smaller tumours and fewer angiogenic islets in comparison to the CatS+/+ control mice (Gocheva et al., 2006). Insight to the molecular mechanism underpinning this phenotype was subsequently provided by evidence that CatS could cleave and inactivate anti-angiogenic peptides and promote the generation of active pro-angiogenic fragments (Wang et al, 2006).

The role of Cat S has also been investigated in specific malignancies. The expression of Cat S was shown to be significantly greater in lung tumour and prostate carcinomas sections in comparison to normal tissue (Kos et al, 2001, Fernandez et al, 2001) and suggested that Cat S may have a role in tumour invasion and disease progression.

Recent work on Cat S demonstrated the significance of its expression in human astrocytomas (Flannery et al, 2003). Immunohistochemical analysis showed the expression of Cat S in a panel of astrocytoma biopsy specimens from WHO grades I to IV, but appeared absent from normal astrocytes, neurones, oligodendrocytes and endothelial cells. Cat S expression appeared highest in grade IV tumours and levels of extracellular activity were greatest in cultures derived from grade IV tumours.

Cat S has been shown to be active in the degradation of ECM macromolecules such as laminin, collagens, elastin and chondroitin sulphate proteoglycans (Liuzzo et al, 1999). Using invasion assays with the U251MG grade IV glioblastoma cell line, a 61% reduction in invasion in the presence of a Cat S inhibitor LHVS29 has been shown (Flannery et al, 2003).

The generation of inhibitors specifically targeting Cat S have potential as therapeutic agents for alleviations of the symptoms associated with the activity of this protease.

The implication of aberrant extracellular cysteine cathepsin activity in tumour progression has been of particular focus to researchers. Each of these lysosomal enzymes has been implicated in the progression of various tumours, where it is thought that their abnormally high secretion from tumour cells leads to the degradation of the extracellular matrix (ECM). This aberrant breakdown of ECM components such as elastin and collagen accelerates the penetration and invasion of these abnormal cells to surrounding normal tissue. Additionally, roles in angiogenesis and the processing of other molecules have also been attributed to inappropriate cathepsin activity (Lah and Kos, 1998 Biol. Chem. 379, 125-30; Folkman and Ingber, 1992; Fernandez et al, 2001).

Much research has focussed on the underlying mechanisms that result in this devastating increase in extracellular proteolytic activity. Cathepsins are believed to be involved in the degradation of the ECM directly through their ability to degrade components of the ECM such as laminin, fibronectin and collagen or indirectly through the activation of other proteases in a proteolytic cascade (Koblinski et al, 2000; Rao et al, 2003).

Inhibition of Cat S

When proteases are over-expressed, therapeutic strategies have focused on the development of inhibitors to block the activity of these enzymes. The generation of specific small molecule inhibitors to the cathepsins have proved difficult in the past, due to problems with selectivity and specificity. The dipeptide α-keto-β-aldehydes developed as potent reversible inhibitors to Cat S by Walker et al, had the ability to inhibit Cat B and L, albeit with less efficiency (Walker et al, *Biochem. Biophys. Res. Comm.* 2000; 75: 401-405), and the Cat S inhibitor 4-Morpholineurea-Leu-HomoPhe-vinylsulphone (LHVS) has also been shown to inhibit other cathepsins when used at higher concentrations (Palmer et al, *J. Med. Chem.* 1995; 38: 3193-3196).

A broad range of antineoplastics have been developed for the treatment of cancer. However, although many of these compounds are successfully used in treatment strategies, in many cases a particular treatment regime does not result in complete clearance of neoplasms or only does so temporarily. There thus remains a great need for the development of new cancer treatments and therapeutic regimes.

SUMMARY OF THE INVENTION

As described herein, the present inventors have unexpectedly found that Cathepsin S (CatS) can be found on the cell surface of tumour cell lines. When a CatS monoclonal antibody was employed as an isotype control in an unrelated tumour treatment study the inventors discovered positive staining of tumour cells with the antibody.

The surprising discovery by the present inventors that, contrary to the commonly held belief in the art that this molecule was localised internally in lysosomes in tumour cells or secreted from such cells, Cathepsin S is localised on the cell surface of tumour cells, provides a means to identify tumour cells in a population of cells.

Accordingly, in a first aspect of the present invention, there is provided a method of identifying a tumour cell in a population of cells, said method comprising bringing into contact a ligand with binding specificity for Cathepsin S with said population of cells and determining the presence or absence of binding of the ligand to cells in said population, wherein binding is indicative of the presence of tumour cells within said population of cells.

The method of the first aspect of the invention may be performed in vitro. In another embodiment, the method is performed in vivo.

The invention also enables the cell-surface CatS to be employed as a biomarker for the use of antibody delivered drug conjugates. This strategy could be further exploited by the delivery of pro-drugs to the cells, which are activated specifically by the enzymatic activity of CatS.

In a second aspect of the present invention, there is provided the use of Cathepsin S as a biomarker for tumour cells.

Moreover, the present inventors have found that treatment of tumour derived cell lines with chemotherapeutic agents leads to enhanced cell surface localisation of Cathepsin S. This implies that the chemotherapy could therefore counter-productively promote the degradation of the ECM, increasing the invasive properties of the aberrant cells. This effect could have severe implications for the prognosis of the patient being treated with such chemotherapy.

However, the efficacy of existing chemotherapeutic agents could be improved by the targeting of this cell surface CatS. Inhibitors to CatS, for example small molecule, peptide/protein, or antibodies, could be used in combination with chemotherapeutic agents to ensure that the chemotherapy does not result in the generation of a sub-population of cells that are hyper-invasive.

Thus, in a third aspect of the present invention, there is provided a method of inhibiting chemotherapy induced upregulation of Cathepsin S on the surface of tumour cells, said method comprising the administration of a Cathepsin S inhibitor to said cells.

In a fourth aspect of the invention there is provided a method of treating neoplastic disease comprising the simultaneous, sequential or separate administration of a Cathepsin S inhibitor and a chemotherapeutic agent.

In a fifth aspect, the invention provides the use of a Cathepsin S inhibitor and a chemotherapeutic agent in the preparation of a medicament for combination therapy by simultaneous, sequential or separate administration of the Cathepsin S inhibitor and chemotherapeutic agent in the treatment of a neoplastic disease.

In a sixth aspect of the invention, there is provided a pharmaceutical composition comprising a Cathepsin S inhibitor and a chemotherapeutic agent.

In one embodiment of the invention the Cathepsin S inhibitor and chemotherapeutic agent are provided in concentrations which produce a synergistic effect.

As described in the Examples, the upregulation of Cathepsin S by chemotherapeutic agents was not limited to one class of antineoplastic but appears to be common to many or all classes. The method of the invention may therefore find use in treatment regimes involving any class of chemotherapeutic agent. For example, chemotherapeutic agents, which may be used in the present invention include platinum based antineoplastics, antimetabolites, nucleoside analogs, thymidylate synthase inhibitors, ortopoisomerase inhibitors.

In one embodiment, the chemotherapeutic agent is a platinum based antineoplastic, for example cisplatin or oxaliplatin.

In another particular embodiment, the chemotherapeutic agent is a thymidylate synthase inhibitor, for example 5-FU.

In another particular embodiment, the chemotherapeutic agent is a topoisomerase inhibitor, for example CPT-11.

Any suitable Cathepsin S inhibitor may be used in the present invention. Such inhibitors may be, for example, small molecule inhibitors, peptides or antibodies, or nucleic acid molecules encoding said peptides or antibodies. In one embodiment, the Cathepsin S inhibitor is a small molecule inhibitor such as a dipeptide α-keto-β-aldehyde or 4-Morpholineurea-Leu-HomoPhe-vinylsulphone (LHVS). In another embodiment, the Cathepsin S inhibitor is an antibody molecule, such as an antibody or antibody fragment.

As detailed in the applicant's co pending international patent application which claims priority from GB0507219.4 and GB0507272.3, WO2006/109045, the present inventors have identified a novel class of Cathepsin S antibodies, the antibodies having potent antiproteolytic activity. Moreover, the antibodies are shown to have significant inhibitory effects on tumour invasion and angiogenesis. The class is exemplified by a monoclonal antibody 1E11 for which the inventors have identified the VH and VL domains and CDRs of the antibody. This is the first demonstration of a Cathepsin S specific antibody directly inhibiting the protease activity of Cathepsin S and thus uniquely enables the use of such antibodies as active therapeutic agents with a wide range of applications from cancer therapeutics to anti-inflammatory agents with high specificity and low toxicity.

Accordingly, in one embodiment of the present invention, the Cathepsin S inhibitor is an antibody molecule, which binds Cathepsin S and inhibits its proteolytic activity. Any antibody molecule capable of inhibiting the proteolytic effect of Cathepsin S may be used in such aspects of the invention.

In an embodiment of the invention, the antibody molecule comprises an antigen binding domain comprising at least one of the CDRs with an amino acid sequence selected from the group consisting of Seq ID No: 1, Seq ID No: 2, Seq ID No: 3, and/or at least one of the CDRs with an amino acid sequence consisting of Seq ID No: 4, Seq ID No: 5 and Seq ID No: 6.

The amino acid sequences corresponding to SEQ ID NOS: 1-6 are as follows:

```
Seq ID No: 1:
SYDMS

Seq ID No: 2:
YITTGGVNTYYPDTVKG

Seq ID No: 3:
HSYFDY

Seq ID No: 4:
RSSQSLVHSNGNTYLH

Seq ID No: 5:
KVSNRFS

Seq ID No: 6:
SQTTHVPPT
```

In an embodiment, the antibody molecule comprises an antigen binding domain comprising at least one, for example at least two or all three of the CDRs with an amino acid sequence selected from the group consisting of Seq ID No: 1, Seq ID No: 2, and Seq ID No: 3, or variants thereof and at least one, for example at least two, for example all three of the CDRs with an amino acid sequence selected from the group consisting of Seq ID No: 4, Seq ID No: 5 and Seq ID No: 6, or variants thereof.

In another embodiment, the antibody molecule comprises an antigen binding domain comprising at least one of the CDRs with an amino acid sequence selected from the group consisting of Seq ID No: 1, Seq ID No: 2, and Seq ID No: 3, and/or at least one of the CDRs with an amino acid sequence selected from the group consisting of Seq ID No: 4, Seq ID No: 5 and Seq ID No: 6.

In a particular embodiment, the antibody molecule comprises a CDR having the amino acid sequence SEQ ID NO: 5, or a variant thereof and/or the CDR having the amino acid sequence SEQ ID NO: 6, or a variant thereof.

In one embodiment, the antibody molecule comprises an antibody $V_H$ domain or an antibody $V_L$ domain, or both.

In one embodiment, the antibody molecule has an antibody $V_H$ domain which comprises at least one of the CDRs, for example two or three CDRs, with an amino acid sequence selected from the group consisting of Seq ID No: 1, Seq ID No: 2, Seq ID No: 3, and/or the antibody $V_L$ domain comprises at least one of the CDRs, for example two or three CDRs, with an amino acid sequence consisting of Seq ID No: 4, Seq ID No: 5 and Seq ID No: 6.

In a preferred embodiment, the antibody $V_L$ domain comprises the amino acid sequence Seq ID No: 8 and/or the antibody $V_H$ domain comprises the amino acid sequence Seq ID No: 7.

```
Seq ID No: 7:
VQLQESGGVLVKPGGSLKLSCAASGFAFSSYDMSWVRQTPEKRLEWVAYI

TTGGVNTYYPDTVKGRFTISRDNAKNTLYLQMSSLKSEDTAMYYCARHSY

FDYWGQGTTVTVSS

Seq ID No: 8:
DVLMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQTTHVP

PTFGSGTKLEIKR
```

The antibody molecule may be an antibody, for example a whole antibody.

In one alternative embodiment, the antibody molecule may be an antibody fragment such as a scFv.

Further antibody molecules which may be used in the present invention include antibody molecules comprising at least one, for example one, two or three, of the CDRs with an amino acid sequence selected from the group consisting of Seq ID No: 1, Seq ID No: 2, Seq ID No: 3, and/or at least one, for example one, two or three, of the CDRs with an amino acid sequence consisting of Seq ID No: 4, Seq ID No: 5 and Seq ID No: 6, in which 5 or less, for example 4, 3, 2, or 1 amino acid substitutions have been made in at least one CDR and wherein the antibody molecule retains the ability to inhibit the proteolytic activity of Cathepsin S.

In an embodiment of the invention, the antibody molecule for use in the invention has the ability to inhibit tumour cell invasion.

In another embodiment, the antibody molecule for use in the invention has the ability to inhibit angiogenesis.

As described above, the present inventors have surprisingly shown that, in tumour cells, Cathepsin S is localised on the cell surface and, moreover, in tumour cells subjected to chemotherapeutic agents, Cathepsin S expression on the surface of the tumour cells, is upregulated. This demonstration, as well as enabling the identification of tumour cells using antibodies against Cathepsin S and the use of combination therapies of a Cathepsin S inhibitor and a chemotherapeutic agent, also suggests that anti-Cathepsin S antibodies may be used in the absence of chemotherapeutic agents to induce ADCC in tumour cells.

Accordingly, in a seventh aspect of the present invention, there is provided a method of inducing antibody dependent cell-mediated cytotoxic (ADCC) reaction against a tumour cell, said method comprising the administration of an anti-Cathepsin S antibody molecule which binds Cathepsin S to said cell.

By inducing ADCC, tumour cells may be killed. Thus, in an eighth aspect of the present invention, there is provided a method of killing tumour cells, said method comprising the administration of an anti-Cathepsin S antibody molecule which binds Cathepsin S to said cells.

The methods of the seventh and eighth aspects of the invention may be performed in vitro, in vivo or ex vivo, as required.

Accordingly, in a ninth aspect of the present invention, there is provided a method of treating neoplastic disease in a subject, said method comprising the administration of an anti-Cathepsin S antibody molecule which binds Cathepsin S to said subject.

In an tenth aspect, the invention provides the use of an anti-Cathepsin S antibody molecule which binds Cathepsin S in the preparation of a medicament for the treatment of a neoplastic disease.

Moreover, the demonstration that Cathepsin S is localised on the surface of tumour cells suggests that, to induce an anti-tumour cell effect, there is no requirement that the antibodies which bind Cathepsin S need have any anti-proteolytic activity.

Thus, in one embodiment of any one of the seventh to tenth aspects of the present invention, the antibody molecule thereof does not inhibit the proteolytic activity of Cathepsin S.

In one embodiment of any one of the seventh to tenth aspects of the present invention, the anti-Cathepsin S antibody molecule is administered in the absence of another chemotherapeutic agent, i.e. in contrast to the methods of any one of the first to sixth aspects of the present invention.

As described above, in the methods of the invention, anti Cathepsin S antibody molecules may be used which do not inhibit the proteolytic effect of Cathepsin S. The therapeutic use of such antibody molecules is further supported by the demonstration by the present inventors, as described in the Examples, of the anti-angiogenic effects of such anti-Cathepsin S antibody molecules.

Specifically, the present inventors have shown for the first time that antibodies, which have specificity for Cathepsin S, but which do not inhibit the proteolytic activity of Cathepsin S, nevertheless act as potent inhibitors of angiogenesis. This was particularly surprising to the inventors given that, as described in PCT/GB2006/001314, it was believed that, to counteract the pathological effects of dysregulation of Cathepsin S activity, strategies are required which inhibit the proteolytic effects of Cathepsin S. Furthermore, although the use of antibodies to sequester proteins has been suggested as a therapeutic strategy for some proteins, e.g. VEGF, such a strategy has not, until now, been considered as feasible for the treatment of diseases associated with Cathepsin S activity.

Accordingly, in an eleventh aspect, the present invention provides a method of treating a condition associated with angiogenesis in a patient in need of treatment thereof, said method comprising administration of an antibody molecule or a nucleic acid encoding said antibody molecule to said patient, wherein said antibody molecule specifically binds Cathepsin S but does not inhibit the proteolytic activity of Cathepsin S.

According to a twelfth aspect of the invention, there is provided the use of an antibody molecule or a nucleic acid encoding said antibody molecule in the preparation of a medicament for the treatment of a condition associated with angiogenesis, wherein said antibody molecule specifically binds Cathepsin S but does not inhibit the proteolytic activity of Cathepsin S.

These aspects of the invention may be used in the treatment of any disease or condition in which angiogenesis plays a part in the pathology of the disease. Such conditions and diseases include, but are not limited to, cancer, inflammatory conditions, for example inflammatory muscle disease, rheumatoid arthritis and asthma, ocular diseases, and atherosclerosis.

Moreover, the demonstration that antibody molecules which specifically bind Cathepsin S but do not inhibit the proteolytic activity of Cathepsin S nevertheless inhibit angiogenesis enables the use of such antibody molecules in the treatment of other conditions associated with Cathepsin S.

In a thirteenth aspect, there is provided a method of treating a condition associated with activity, for example aberrant activity of Cathepsin S in a patient in need of treatment thereof, said method comprising administration of an antibody molecule or a nucleic acid encoding said antibody molecule, wherein said antibody molecule specifically binds Cathepsin S but does not inhibit the proteolytic activity of Cathepsin S.

Also provided as a fourteenth aspect is the use of an antibody molecule or a nucleic acid encoding said antibody molecule in the preparation of a medicament for the treatment of a condition associated with aberrant activity of Cathepsin S, wherein said antibody molecule specifically binds Cathepsin S but does not inhibit the proteolytic activity of Cathepsin S.

As well as the treatment of tumours, the invention may be used in the treatment of any condition with which aberrant activity of Cathepsin S is associated, in particular conditions associated with aberrant expression of Cathepsin S. In one embodiment, a condition is considered to be associated with aberrant activity of Cathepsin S if the proteolytic activity of Cathepsin S is greater than in the absence of said condition, for example wherein the proteolytic activity is at least 20% greater, for example at least 50% greater, such as at least 100% greater, at least 200% greater or at least 500% greater than in the absence of said condition. In one embodiment, a condition is considered to be associated with aberrant expression of Cathepsin S if the expression of Cathepsin S is greater than in the absence of said condition, for example wherein the expression is at least 20% greater, for example at least 50% greater, such as at least 100% greater, at least 200% greater or at least 500% greater than in the absence of said condition.

For example, conditions in which the invention may be used include, but are not limited to neurodegenerative disorders, for example Alzheimer's disease and multiple sclerosis, autoimmune disorders, and other diseases associated with excessive, deregulated or inappropriate angiogenesis.

In any of the eleventh to fourteenth aspects of the present invention, any suitable anti-Cathepsin S antibody molecule, which does not inhibit the proteolytic activity of Cathepsin S, but which inhibits angiogenesis, may be used.

Such antibody molecules and nucleic acids encoding such antibody molecules constitute, a fifteenth independent aspect of the invention.

In one embodiment of the fifteenth aspect of the invention, the antibody molecule is a 1E4 antibody or a fragment or variant thereof. Such fragments and variants preferably retain the ability to inhibit angiogenesis but do not have ability to inhibit the proteolytic activity of Cathepsin S.

In one embodiment of the invention, the antibody molecule of and for use in the invention has the ability to inhibit tumour cell invasion.

According to a sixteenth aspect of the invention, there is provided an antibody molecule or a nucleic acid encoding said antibody molecule for use in medicine, wherein said antibody molecule specifically binds Cathepsin S but does not inhibit the proteolytic activity of Cathepsin S Also provided by the invention as a seventeenth aspect is the use of an antibody molecule or a nucleic acid encoding said antibody molecule, in the preparation of a medicament for the treatment of a condition associated with activity of Cathepsin S, wherein said antibody molecule specifically binds Cathepsin S but does not inhibit the proteolytic activity of Cathepsin S in the preparation of a medicament for the treatment of a condition associated with activity of Cathepsin S.

Another aspect of the invention is a pharmaceutical composition comprising an antibody molecule or a nucleic acid encoding said antibody molecule, wherein said antibody molecule specifically binds Cathepsin S, but does not inhibit the proteolytic activity of Cathepsin S.

Preferred features of each aspect of the invention are as for each of the other aspects mutatis mutandis unless the context demands otherwise.

DETAILED DESCRIPTION

Cathepsin S Inhibitors

As described above, any suitable Cathepsin S inhibitor may be used in the present invention. The inhibitor may be, for example a small molecule pharmaceutical, for example dipeptide α-keto-β-aldehydes The dipeptide α-keto-β-aldehydes were developed as potent reversible inhibitors to Cat S by Walker et al, and have been shown to inhibit Cat B and L, albeit with less efficiency (Walker et al, 2000). Another small molecule inhibitor of Cathepsin S which may be used in the present invention is 4-Morpholineurea-Leu-HomoPhe-vinyl-sulphone (LHVS). Other Cathepsin S inhibitors which may be used are for example the non-peptide Cathepsin S inhibitors described in Thurmond et al, J Med Chem. 2004 Sep. 23; 47 (20): 4799-801.

In another embodiment, the Cathepsin S inhibitor is an antibody molecule, such as an antibody or antibody fragment.

In the context of the present invention, an "antibody" should be understood to refer to an immunoglobulin or part thereof or any polypeptide comprising a binding domain which is, or is homologous to, an antibody binding domain. Antibodies include but are not limited to polyclonal, monoclonal, monospecific, polyspecific antibodies and fragments thereof and chimeric antibodies comprising an immunoglobulin binding domain fused to another polypeptide.

Intact (whole) antibodies comprise an immunoglobulin molecule consisting of heavy chains and light chains, each of which carries a variable region designated VH and VL, respectively. The variable region consists of three complementarity determining regions (CDRs, also known as hypervariable regions) and four framework regions (FR) or scaffolds. The CDR forms a complementary steric structure with the antigen molecule and determines the specificity of the antibody.

Fragments of antibodies may retain the binding ability of the intact antibody and may be used in place of the intact antibody. Accordingly, for the purposes of the present invention, unless the context demands otherwise, the term "antibodies" should be understood to encompass antibody fragments. Examples of antibody fragments include Fab, Fab', F (ab')2, Fd, dAb, and Fv fragments, scFvs, bispecific scFvs, diabodies, linear antibodies (see U.S. Pat. No. 5,641,870, Example 2; Zapata et al., Protein Eng 8 (10): 1057-1062 [1995]); single-chain antibody molecules; and multispecific antibodies formed from antibody fragments.

The Fab fragment consists of an entire L chain (VL and CL), together with VH and CH1. Fab' fragments differ from Fab fragments by having additional few residues at the carboxy terminus of the CH1 domain including one or more cysteines from the antibody hinge region. The F (ab')2 fragment comprises two disulfide linked Fab fragments.

Fd fragments consist of the VH and CH1 domains.

Fv fragments consist of the VL and VH domains of a single antibody.

Single-chain Fv fragments are antibody fragments that comprise the VH and VL domains connected by a linker which enables the scFv to form an antigen binding site. (see Pluckthun in The Pharmacology of Monoclonal Antibodies, vol. 113, Rosenburg and Moore eds., Springer-Verlag, New York, pp. 269-315 (1994).

Diabodies are small antibody fragments prepared by constructing scFv fragments (see preceding paragraph) with short linkers (about 5-10 residues) between the VH and VL domains such that inter-chain but not intra-chain pairing of the V domains is achieved, resulting in a multivalent fragment, i.e. a fragment having two antigen-binding sites (see, for example, EP 404 097; WO 93/11161; and Hollinger et al., Proc. Natl. Acad. Sci. USA, 90: 6444-6448 (1993))

Further encompassed by fragments are individual CDRs.

In one embodiment of the present invention, the Cathepsin S inhibitor is an antibody molecule. In some embodiments of the invention, the antibody molecule is an antibody molecule which inhibits the proteolytic activity of Cathepsin S. An example of such a suitable binding agent is the antibody 1E11 as described herein and in the applicant's copending international patent application, WO2006/109045, claiming priority from GB0507219.4 and GB0507272.3. The inventors have identified the amino acid sequences of the VH and VL regions of the intact antibody 1E11. Furthermore, the inventors have identified the six CDRs of this antibody (Seq ID Nos: 1, 2, 3, 4, 5 and 6).

As described above, the antibody molecules for use in any one of the first to tenth aspects of the present invention are not limited to antibodies having the specific sequences of the 1E11 antibody, the VH, VL and the CDRs having the sequences disclosed herein but also extends, for example, to any other antibody which inhibits Cathepsin S proteolytic activity. For example variants of 1E11, which maintain the ability to inhibit the proteolytic activity of Cat S may be used in some embodiments of the invention. Thus, the CDR amino acid sequences of the 1E11 antibody, in which one or more amino acid residues are modified may also be used as the CDR sequence. The modified amino acid residues in the amino acid sequences of the CDR variant are preferably 30% or less, more preferably 20% or less, most preferably 10% or less, within the entire CDR. Such variants may be provided using the teaching of the present application and techniques known in the art. The CDRs may be carried in a framework structure comprising an antibody heavy or light chain sequence or part thereof. Preferably such CDRs are positioned in a location corresponding to the position of the CDR(s) of naturally occurring VH and VL domains. The positions of such CDRs may be determined as described in Kabat et al, Sequences of Proteins of Immunological Interest, US Dept of Health and Human Services, Public Health Service, Nat'l Inst. of Health, NIH Publication No. 91-3242, 1991.

Furthermore, modifications may alternatively or additionally be made to the Framework Regions of the variable regions. Such changes in the framework regions may improve stability and reduce immunogenicity of the antibody.

However, as described above and as shown in the Examples, the present inventors have also shown that anti-angiogenic effects may be achieved using antibody molecules which bind Cathepsin S but which do not inhibit the proteolytic activity of Cathepsin S. Such antibody molecules may be used in any aspect of the present invention.

Antibodies for use in the invention herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81: 6851-6855 (1984)). Chimeric antibodies of interest herein include "primatized" antibodies comprising variable domain antigen-binding sequences derived from a non-human primate (e.g. Old World Monkey, Ape etc), and human constant region sequences.

Antibody molecules for use in the present invention may be produced in any suitable way, either naturally or synthetically. Such methods may include, for example, traditional hybridoma techniques (Kohler and Milstein (1975) Nature, 256: 495-499), recombinant DNA techniques (see e.g. U.S. Pat. No. 4,816,567), or phage display techniques using antibody libraries (see e.g. Clackson et al. (1991) Nature, 352: 624-628 and Marks et al. (1992) Bio/Technology, 10: 779-783). Other antibody production techniques are described in Using Antibodies: A Laboratory Manual, eds. Harlow et al., Cold Spring Harbor Laboratory, 1999.

Traditional hybridoma techniques typically involve the immunisation of a mouse or other animal with an antigen in order to elicit production of lymphocytes capable of binding the antigen. The lymphocytes are isolated and fused with a myeloma cell line to form hybridoma cells which are then cultured in conditions which inhibit the growth of the parental myeloma cells but allow growth of the antibody producing cells. The hybridoma may be subject to genetic mutation, which may or may not alter the binding specificity of antibodies produced. Synthetic antibodies can be made using techniques known in the art (see, for example, Knappik et al, J. Mol. Biol. (2000) 296, 57-86 and Krebs et al, J. Immunol. Meth. (2001) 2154 67-84.

Modifications may be made in the VH, VL or CDRs of the binding members, or indeed in the FRs using any suitable technique known in the art. For example, variable VH and/or VL domains may be produced by introducing a CDR, e.g. CDR3 into a VH or VL domain lacking such a CDR. Marks et al. (1992) Bio/Technology, 10: 779-783 describe a shuffling technique in which a repertoire of VH variable domains lacking CDR3 is generated and is then combined with a CDR3 of a particular antibody to produce novel VH regions. Using analogous techniques, novel VH and VL domains comprising CDR derived sequences of the present invention may be produced.

Accordingly, antibody molecules for use in the invention may be produced by a method comprising: (a) providing a starting repertoire of nucleic acids encoding a variable domain, wherein the variable domain includes a CDR1, CDR2 or CDR3 to be replaced or the nucleic acid lacks an encoding region for such a CDR; (b) combining the repertoire with a donor nucleic acid encoding an amino acid sequence having the sequence as shown as Seq ID No: 1, 2, 3, 4, 5 or 6 herein such that the donor nucleic acid is inserted into the CDR region in the repertoire so as to provide a product repertoire of nucleic acids encoding a variable domain; (c) expressing the nucleic acids of the product repertoire; (d) selecting a specific antigen-binding fragment specific for CatS; and (e) recovering the specific antigen-binding fragment or nucleic acid encoding it. The method may include an optional step of testing the antibody molecule for ability to inhibit the proteolytic activity of Cathepsin S.

Alternative techniques of producing antibodies for use in the invention may involve random mutagenesis of gene(s) encoding the VH or VL domain using, for example, error prone PCR (see Gram et al, 1992, P.N.A.S. 89 3576-3580. Additionally or alternatively, CDRs may be targeted for mutagenesis e.g. using the molecular evolution approaches described by Barbas et al 1991 PNAS 3809-3813 and Scier 1996 J Mol Biol 263 551-567.

Having produced such variants, antibodies and fragments may be tested for binding to Cat S and for the ability to inhibit the proteolytic activity of Cathepsin S.

As described herein, the inventors have demonstrated that antibody molecules which may be used in some aspects of the present invention have an anti-proteolytic effect. Furthermore anti-invasive and anti-angiogenic activity has also been demonstrated, as described in the Examples. This therefore enables the use of the antibody molecules of the invention as active therapeutic agents. An antibody molecule for use in the invention may be a "naked" antibody molecule. A "naked" antibody molecule is an antibody molecule which is not conjugated with an "active therapeutic agent". In the context of the present application, an "active therapeutic agent" is a molecule or atom which is conjugated to an antibody moiety (including antibody fragments, CDRs etc) to produce a conjugate. Examples of such "active therapeutic agents" include drugs, toxins, radioisotopes, immunomodulators, chelators, boron compounds, dyes etc.

Immunoconjugates

In another embodiment of the invention, an antibody molecule for use in some embodiments of the invention may be in the form of an immunoconjugate, comprising an antibody fragment conjugated to an "active therapeutic agent". The therapeutic agent may be a chemotherapeutic agent or another molecule.

Methods of producing immunoconjugates are well known in the art; for example, see U.S. Pat. No. 5,057,313, Shih et al., Int. J. Cancer 41: 832-839 (1988); Shih et al., Int. J. Cancer 46: 1101-1106 (1990), Wong, Chemistry Of Protein Conjugation And Cross-Linking (CRC Press 1991); Upeslacis et al., "Modification of Antibodies by Chemical Methods" in Monoclonal Antibodies: Principles And Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering And Clinical Application, Ritter et al. (eds.), pages 60-84 (Cambridge University Press 1995).

In those aspects of the present invention, where it is desired to employ a combination of a Cathepsin S inhibitor and a chemotherapeutic, an immunoconjugate comprising an anti-Cathepsin S antibody and a chemotherapeutic agent may be used.

Such immunoconjugates will have a number of advantages over conventional treatments. The demonstration that Cathepsin S is localised on tumour cells enables the use of such immunoconjugates to target chemotherapeutic agents to tumour cells. The targeted chemotherapeutic agent may have its cytotoxic effect. Secondly, as described above, it has been found that conventionally used chemotherapeutics cause upregulation of Cathepsin S on the cell surface of tumour cells, for example colorectal tumour cells. By employing an immunoconjugate of an anti-Cathepsin S antibody and a chemotherapeutic agent, the Cathepsin S antibody part of the immunoconjugate is expected to counteract this effect. Moreover, the antibody portion of the immunoconjugate would be expected to have a longer active half life in the body than the chemotherapeutic agent and so may counteract the effects of the Cathepsin S upregulation caused by the chemotherapeutic agent to which it was attached.

An immunoconjugate of an anti-Cathepsin S antibody molecule and a chemotherapeutic agent forms a further aspect of the present invention. In one embodiment, the antibody molecule is cleavable from the chemotherapeutic agent by a protease, for example, a Cathepsin.

The antibody molecules for use in the invention may comprise further modifications. For example the antibodies can be glycosylated, pegylated, or linked to albumin or a nonproteinaceous polymer. The antibody molecule may be in the form of an immunoconjugate.

The ability of an agent, for example a small molecule or antibody, to inhibit the proteolytic activity of Cathepsin S may be tested using any suitable method. For example a fluorimetric assay may be used. In such an assay, any suitable fluorigenic substrate may be used, for example Cbz-Phe-Arg-AMC. An agent is considered to inhibit the proteolytic activity of Cathepsin S if it has the ability to inhibit its activity by a statistically significant amount. For example, in one embodiment, an agent for use as the Cathepsin S inhibitor is able to inhibit the inhibitory activity by at least 10%, for example at least 25%, 50%, 70%, 80% or 90%, when compared to an appropriate control antibody.

The ability of an agent to inhibit tumour cell invasion may be tested using any suitable invasion assay known in the art. For example, such ability may be tested using a modified Boyden chamber as is known in the art. The antibody molecule may be tested using any suitable tumour cell line, for example a prostate carcinoma cell line, e.g. pC3, an astrocytoma cell line e.g. U251mg, a colorectal carcinoma cell line, e.g. HCT116, or a breast cancer cell line, e.g. MDA-MB-231 or MCF7. An agent may be considered to inhibit tumour cell invasion if it has the ability to inhibit invasion by a statistically significant amount. For example, in one embodiment, an agent for use as the Cathepsin S inhibitor is able to inhibit invasion by at least 10%, for example at least 25%, 50%, 70%, 80% or 90% when compared to an appropriate control antibody.

The ability of an agent to inhibit angiogenesis may be tested using any suitable assay known in the art. For example, such ability may be tested using the assays described in the Assay section and/or as described in the Examples, for example a Matrigel based assay.

In certain aspects of the invention, for example in assays to determine the presence of tumour cells in a population of cells or in diagnostic techniques to determine the presence of cells in vivo, labelled antibody molecules may be used. Labels which may be used include radiolabels, enzyme labels such as horseradish peroxidase, alkaline phosphatase, or biotin.

Nucleic Acid

Nucleic acid for use in the present invention may comprise DNA or RNA. It may be produced recombinantly, synthetically, or by any means available to those in the art, including cloning using standard techniques.

The nucleic acid may be inserted into any appropriate vector, for example a virus (e.g. vaccinia virus, adenovirus, etc.), baculovirus; yeast vector, phage, chromosome, artificial chromosome, plasmid, or cosmid DNA. Vectors may be used to introduce the nucleic acids into a host cell, which may be prokaryotic or eukaryotic.

For further details relating to known techniques and protocols for manipulation of nucleic acid, for example, in preparation of nucleic acid constructs, mutagenesis, sequencing, introduction of DNA into cells and gene expression, and analysis of proteins, see, for example, Current Protocols in Molecular Biology, 5th ed., Ausubel et al. eds., John Wiley & Sons, 2005 and, Molecular Cloning: a Laboratory Manual: $3^{rd}$ edition Sambrook et al., Cold Spring Harbor Laboratory Press, 2001.

Chemotherapeutic Agents

As described above, in some embodiments of the invention, chemotherapeutic agents may be used, for example in combination treatment regimes with Cathepsin S inhibitors. In such embodiments, any suitable chemotherapeutic agent may be used in the present invention. For example agents which may be used include antimetabolites, nucleoside analogs, thymidylate synthase inhibitors, platinum cytotoxic agents or topoisomerase inhibitors. Examples of thymidylate synthase inhibitors which may be used in the invention include 5-FU, MTA and TDX. In one embodiment, the thymidylate synthase inhibitor is 5-FU. An example of an antimetabolite which may be used is tomudex (TDX). Examples of platinum cytotoxic agents which may be used include cisplatin and oxaliplatin. In one embodiment of the invention, the chemotherapeutic agent is cisplatin. Any suitable topoisomerase inhibitor may be used in the present invention. Examples of nucleoside analogs which may be used include but are not limited to gemcitabine and cytarabine.

In a particular embodiment of the invention, the chemotherapeutic agent is a topoisomerase inhibitor.

Any suitable topoisomerase inhibitor may be used in the present invention. In a particular embodiment, the topoisomerase inhibitor is a topoisomerase I inhibitor, for example a camptothecin. A suitable topoisomerase I inhibitor, which may be used in the present invention is irenotecan (CPT-11) or its active metabolite SN-38. CPT-11 specifically acts in the S phase of the cell cycle by stabilizing a reversible covalent reaction intermediate, referred to as a cleavage or cleavage complex and may also induces $G_2$-M cell cycle arrest.

Chemotherapeutic agents which may be used in the present invention in addition or instead of the specific agents recited above, may include alkylating agents; alkyl sulfonates; aziridines; ethylenimines; methylamelamines; nitrogen mustards; nitrosureas; anti-metabolites; folic acid analogues; purine analogs; pyrimidine analogs; androgens; anti-adrenals; folic acid replenishers; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; ionidamine; mitoguazone; mitoxantrone In a particular embodiment of the invention, the chemotherapeutic agent is a fluoropyrimidine, e.g. 5-FU, or a metabolite thereof. 5-FU is used in the treatment of many cancers, including gastrointestinal, breast and head and neck cancers. 5-FU is converted intracellularly to fluorodeoxyuridine monophosphate FdUMP, which, together with 5,10-methylene tetrahydrofolate ($CH_2THF$) forms a stable ternary complex with thymidylate synthase (TS), resulting in enzyme inhibition. TS catalyses the reductive methylation of deoxyuridine monophosphate (dUMP) by $CH_2THF$ to produce deoxythymidine monophosphate (dTMP) and dihydrofolate (Longley et al Nat Rev Cancer, 3: 330-338, 2003). As this reaction provides the sole de novo intracellular source of dTMP, which is essential for DNA replication and repair, TS inhibition results in DNA damage. Non-TS-directed mechanisms of cytotoxicity have also been described for 5-FU, such as misincorporation of fluoronucleotides into DNA and RNA (Longley et al Nat Rev Cancer, 3: 330-338, 2003).

Where reference is made to specific chemotherapeutic agents, it should be understood that analogues including biologically active derivatives and substantial equivalents thereof, which retain the antitumour activity of the specific agents, may be used.

Treatment

Treatment" includes any regime that can benefit a human or non-human animal. The treatment may be in respect of an existing condition or may be prophylactic (preventative treatment). Treatment may include curative, alleviation or prophylactic effects.

"Treatment of cancer" includes treatment of conditions caused by cancerous growth and/or vascularisation and includes the treatment of neoplastic growths or tumours. Examples of tumours that can be treated using the invention are, for instance, sarcomas, including osteogenic and soft tissue sarcomas, carcinomas, e.g., breast-, lung-, bladder-, thyroid-, prostate-, colon-, rectum-, pancreas-, stomach-, liver-, uterine-, prostate, cervical and ovarian carcinoma, non-small cell lung cancer, hepatocellular carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, astrocytomas, gliomas and retinoblastomas.

In one embodiment, the present invention may be used to treat colorectal tumours.

The invention may be particularly useful in the treatment of existing cancer and in the prevention of the recurrence of cancer after initial treatment or surgery.

Pharmaceutical Compositions

Pharmaceutical compositions according to the present invention, and for use in accordance with the present invention may comprise, in addition to active ingredients, a pharmaceutically acceptable excipient, a carrier, buffer stabiliser or other materials well known to those skilled in the art (see, for example, (Remington: the Science and Practice of Pharmacy, $21^{st}$ edition, Gennaro A R, et al, eds., Lippincott Williams & Wilkins, 2005). Such materials may include buffers such as acetate, Tris, phosphate, citrate, and other organic acids; antioxidants; preservatives; proteins, such as serum albumin, gelatin, or immunoglobulins; hydrophilic polymers such aspolyvinylpyrrolidone; amino acids such as glycine, glutamine, asparagine, histidine, arginine, or lysine; carbohydrates; chelating agents; tonicifiers; and surfactants.

The pharmaceutical compositions may also contain one or more further active compounds selected as necessary for the particular indication being treated, preferably with complementary activities that do not adversely affect the activity of the composition of the invention. For example, in the treatment of cancer, where a combination regime is being used, in addition to a Cathepsin S inhibitor, for example an anti Cathepsin S antibody molecule and a chemotherapeutic agent, the formulation or kit may comprise an additional component, for example a second or further Cathepsin S inhibitor, a second or further chemotherapeutic agent, or an antibody to a target other than Cathepsin S, for example to a growth factor which affects the growth of a particular cancer.

The active ingredients (e.g. antibody molecules and/or chemotherapeutic agents) may be administered via microspheres, microcapsules liposomes, other microparticulate delivery systems. For example, active ingredients may be entrapped within microcapsules which may be prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nanoparticles and nanocapsules) or in macroemulsions. For further details, see Remington: the Science and Practice of Pharmacy, $21^{st}$ edition, Gennaro A R, et al, eds., Lippincott Williams & Wilkins, 2005.

Sustained-release preparations may be used for delivery of active agents. Suitable examples of sustained-release preparations include semi-permeable matrices of solid hydrophobic polymers containing the antibody, which matrices are in the form of shaped articles, e.g. films, suppositories or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L glutamate, non-degradable ethylene-vinyl acetate, degradable lactic acid-glycolic acid copolymers, and poly-D-(–)-3-hydroxybutyric acid.

As described above nucleic acids may also be used in methods of treatment. Nucleic acid for use in the invention may be delivered to cells of interest using any suitable technique known in the art. Nucleic acid (optionally contained in a vector) may be delivered to a patient's cells using in vivo or ex vivo techniques. For in vivo techniques, transfection with viral vectors (such as adenovirus, Herpes simplex I virus, or adeno-associated virus) and lipid-based systems (useful lipids for lipid-mediated transfer of the gene are DOTMA, DOPE and DC-Chol, for example) may be used (see for example, Anderson et al., Science 256: 808-813 (1992). See also WO 93/25673).

In ex vivo techniques, the nucleic acid is introduced into isolated cells of the patient with the modified cells being administered to the patient either directly or, for example, encapsulated within porous membranes which are implanted into the patient (see, e.g. U.S. Pat. Nos. 4,892,538 and 5,283, 187). Techniques available for introducing nucleic acids into viable cells may include the use of retroviral vectors, liposomes, electroporation, microinjection, cell fusion, DEAE-dextran, the calcium phosphate precipitation method, etc.

The binding member, agent, product or composition may be administered in a localised manner to a tumour site or other desired site or may be delivered in a manner in which it targets tumour or other cells. Targeting therapies may be used to deliver the active agents more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Kits

The invention further extends to a pharmaceutical kit comprising a Cathepsin S inhibitor and a chemotherapeutic agent for combination therapy by simultaneous, sequential or separate administration of the Cathepsin S inhibitor and chemotherapeutic agent, optionally with instructions for the administration of (a) and (b) separately, sequentially or simultaneously.

Dose

The Cathepsin S inhibitors, anti-Cathepsin S antibodies and/or chemotherapeutic agents of and for use in the invention, as appropriate, are suitably administered to an individual in a "therapeutically effective amount", this being sufficient to show benefit to the individual. The actual dosage regimen will depend on a number of factors including the condition being treated, its severity, the patient being treated, the agents being used, and will be at the discretion of the physician.

In embodiments, in which both a Cathepsin S inhibitor and a chemotherapeutic agent are employed in a combination treatment regime, the Cathepsin S inhibitor and chemotherapeutic agent may be administered simultaneously, separately or sequentially with the chemotherapeutic agent. Where administered separately or sequentially, they may be administered within any suitable time period e.g. within 1, 2, 3, 6, 12, 24, 48 or 72 hours of each other. In preferred embodiments, they are administered within 6, preferably within 2, more preferably within 1, most preferably within 20 minutes of each other.

In one embodiment, in which both a Cathepsin S inhibitor and a chemotherapeutic agent are employed in a combination treatment regime, the Cathepsin S inhibitor and chemotherapeutic agent are administered in doses which produce a synergistic effect.

i.e. administered in a potentiating ratio. The term "potentiating ratio" in the context of the present invention is used to indicate that the Cathepsin S inhibitor and chemotherapeutic agent are present in a ratio such that the cytotoxic activity of the combination is greater than that of either component alone or of the additive activity that would be predicted for the combinations based on the activities of the individual components.

Thus in a potentiating ratio, the individual components act synergistically.

Synergism may be defined using a number of methods.

For example, synergism may be defined as an RI of greater than unity using the method of Kern (Cancer Res, 48: 117-121, 1988) as modified by Romaneli (Cancer Chemother Pharmacol, 41: 385-390, 1998). The RI may be calculated as the ratio of expected cell survival (Se/defined as the product of the survival observed with drug A alone and the survival observed with drug B alone) to the observed cell survival (Sobs) for the combination of A and B (RI=Sexp/Sobs).

Synergism may then be defined as an RI of greater than unity.

In another method, synergism may be determined by calculating the combination index (CI) according to the method of Chou and Talalay (Adv Enzyme Regul, 22: 27-55, 1984). CI values of 1, <1, and >1 indicate additive, synergistic and antagonistic effects respectively.

In an embodiment of the invention, the Cathepsin S inhibitor and the chemotherapeutic agent are present in concentrations sufficient to produce a CI of less than 1, preferably less than 0.85.

Synergism is preferably defined as an RI of greater than unity using the method of Kern as modified by Romaneli (1998a, b). The RI may be calculated as the ratio of expected cell survival (Sep, defined as the product of the survival observed with drug A alone and the survival observed with drug B alone) to the observed cell survival (Sobs) for the combination of A and B(RI=Se/Sobs). Synergism may then be defined as an RI of greater than unity.

In an embodiment of the invention, said Cathepsin S inhibitor and chemotherapeutic agent are provided in concentrations sufficient to produce an RI of greater than 1.5, for example greater than 2.0, such as greater than 2.25.

In one embodiment of the invention, the combined medicament thus produces a synergistic effect when used to treat tumour cells.

Assays

The determination that Cathepsin S is upregulated on the cell surface of tumour cells in response to chemotherapeutic agents enables the provision of assays to determine whether or not a chemotherapeutic agent is having such an effect in a tissue of a patient.

Thus, in a further aspect of the present invention, there is provided a method for evaluating in vitro the response of tumour cells from a subject to the presence of a chemotherapeutic agent to predict response of the tumour cells in vivo to treatment with the chemotherapeutic agent which method comprises: (a) providing an in vitro sample from a subject containing tumour cells; (b) exposing a portion of said sample of tumour cells to said chemotherapeutic agent; (c) comparing expression of Cathepsin S on the surface of said cells with expression of Cathepsin S in a control portion of said sample which has not been exposed to said chemotherapeutic agent; wherein enhanced expression in the portion of sample exposed to said chemotherapeutic agent is indicative of sensitivity to said chemotherapeutic agent.

In preferred embodiments of this aspect of the invention, expression in the sample exposed to said chemotherapeutic agent is considered to be enhanced if the expression is at least 3-fold, preferably at least 4-fold, more preferably at least 5-fold, even more preferably at least 7-fold, yet more preferably at least 10-fold, most preferably at least 12-fold that of the one or more genes in the control portion of said sample which has not been exposed to said chemotherapeutic agent.

Such an assay may be used to determine the suitability of combination therapy using chemotherapeutic agent and a Cathepsin S inhibitor in a particular patient.

The method may alternatively or additionally be used to monitor disease progression, for example using biopsy samples at different times. In such embodiments, instead of comparing the expression of Cathepsin S against a control sample which has not been exposed to said chemotherapeutic agent, the expression of Cathepsin S is compared against a sample obtained from the same tissue at an earlier time point, for example from days, weeks or months earlier.

The nature of the tumour or cancer will determine the nature of the sample which is to be used in the methods of the invention. The sample may be, for example, a sample from a tumour tissue biopsy, bone marrow biopsy or circulating tumour cells in e.g. blood. Alternatively, e.g. where the tumour is a gastrointestinal tumour, tumour cells may be isolated from faeces samples. Other sources of tumour cells may include plasma, serum, cerebrospinal fluid, urine, interstitial fluid, ascites fluid etc.

For example, solid tumours may be collected in complete tissue culture medium with antibiotics.

Cells may be manually teased from the tumour specimen or, where necessary, are enzymatically disaggregated by incubation with collagenase/DNAse and suspended in appropriate media containing, for example, human or animal sera.

In other embodiments, biopsy samples may be isolated and frozen or fixed in fixatives such as formalin. The samples may then be tested for expression levels of genes at a later stage.

In some embodiments of the invention, the effect of a Cathepsin S antibody molecule or combination treatments on cell viability, proliferation or angiogenesis may be desired to be testes. These effects may be tested using any methods known in the art. Some suitable assays are described in the Examples. Others include:

Cell Viability and Proliferation Assays

Cytotoxic and proliferative effects of an antibody on tumour cells may be tested, for example, on U251mg astrocytoma cells can be tested as previously described. Briefly, cells are added to a final concentration of $1 \times 10^4$ cells/200 µl per well of a 96-well microtiter plate (Corning Costar). Appropriate concentrations of monoclonal antibody (100 nM) or vehicle-only control media are added. Plates are incubated at 37° C. and 5% $CO_2$ for 24, 48, 72 and 96 hrs respectively. After incubation, 10 µl of 10 mg/ml MTT is added and incubated for a further 2 h at 37° C. and 5% $CO_2$. The medium is carefully removed and formazan crystals dissolved in 100 µl/well of DMSO. Absorbance is measured as described above and the results expressed as the percentage of cell viability and proliferation relative to each vehicle-only control. All tests are performed in quadruplicate.

A number of assays may be used to investigate the effects of a molecule on angiogenesis. In the Examples, the aortic ring model is described. Others include:

Wound Assay

This in vitro migration is a modified version of the method described by Ashton et al (1999). HMEC-1 is plated into individual chambers on a glass slide and grown to 90% confluence overnight. The medium is removed and the monolayer wounded. The monolayer is re-supplemented with fresh medium and the required volume of antibodies added to give the required final concentration.

Slides are removed at fixed time points until complete closure of the wound, then fixed in 4% PBS buffered paraformaldehyde. The extent of "wound" closure is blindly assessed microscopically by an independent investigator and quantified using a calibrated eyepiece graticule (1 mm/100 µm graduation) at 20× magnification (Olympus BX 50). The extent of closure in the antibody treated slides is compared to time matched sham treated controls and the % inhibition of wound closure compared to time matched controls calculated.

Sponge Assay

Polyether sponges are subcutaneously implanted in C57 black mice and injected on alternate days with 10 ng bFGF or 10 ng bFGF+ antibodies. After 14 days of treatment, sponges are harvested, sectioned and stained with H&E (A).

Oxygen-Induced Retinopathy (OIR) Neonatal Mouse Model

The animal model of oxygen-induced retinopathy employed in this investigation is that described by Smith et al and now widely used for studies testing anti-angiogenic therapies for retinal neovascularisation (Smith et al., 1994). Litters of postnatal mice and their nursing dams are placed in 75% oxygen at postnatal day 7 (P7) and returned to room air at P12. During the 5-day period of hyperoxia the central retinal capillary beds undergo vascular regression and halted development. Upon return to room air the central retina becomes measurably hypoxic with an associated increase in vasogenic growth factors of the VEGF family. An aggressive neovascular response ensues with extra-retinal new vessels developing by P15. Neovascularization is maximal at P17 and regresses after P21.

Unfixed neural retina are dissected and subjected to ultrasonic disruption in RIPA buffer. For quantification of HP-protein binding, retinal samples from P13 and P17 mice are prepared for a HP competitive enzyme-linked immunosorbent assay (ELISA) methodology. Briefly, 100 µl of sample or standard in duplicate are serially diluted in PBS/5% Tween 20 in a 96-well polystyrene assay plate (Corning Inc., Corning, N.Y.) and incubated with 25 µl of rabbit polyclonal antibody against HP (1:3300 in PBS/5% Tween) for 1 hour at 37° C. The contents of each well is then transferred to NUNC C96 Maxisorp plates that are precoated with solid phase antigen (1:5000 in carbonate buffer, pH 9.6) overnight at 4° C. and blocked with 1% gelatin for 1 hour. The competition between solid phase and soluble antigens proceeds for 1 hour at 37° C., after which the wells are washed 4×5 minutes with PBS/5% Tween, and 100 µl of 1:2000 alkaline-phosphatase goat anti-rabbit IgG (Sigma-Aldrich) is added to each well. Plates are then washed 4×5 minutes with PBS/5% Tween, and 100 µl of 1 mg/ml of the alkaline-phosphatase substrate, 4-nitrophenyl phosphate disodium salt hexahydrate (Sigma-Aldrich) dissolved in 10% diethanolamine buffer (pH 9.6) is added to each well. The color development of the subsequent reaction is measured at 405 nm every 5 minutes for 2 hours on a Safire microplate reader (Tecan Instruments) and reaction kinetics analyzed using Magellan 3 software. Sample HP-1 binding is determined by comparison to a Lineweaver-Burk enzyme kinetic standard curve, and is expressed as a proportion of sample protein concentration. The solid-phase antigen used in the assay is HP, which is reductively bound to bovine serum albumin. Statistical analysis is conducted using the Student's t-test and a P value <0.05 is considered significant.

BRIEF DESCRIPTION OF THE DRAWINGS

The invention will now be described further in the following non-limiting examples. Reference is made to the accompanying drawings in which:

FIG. 15a shows photographs of HMEC cells cultured in vehicle only control, an isotype control, an anti Cathepsin S antibody (mAb1), or an anti Cathepsin S antibody (mAb2);

FIG. 15b illustrates graphs illustrating the inhibition of capillary cell branching observed in the presence of 1E11 (upper panel) or 1E4 (lower panel).

FIG. 16a illustrates photographs of sections of aorta cultured in the presence of a control antibody and anti Cathepsin S antibody 1E11 at 60, 300 and 600 nM concentrations.

FIG. 16b (top left) illustrates graph summarising the effect of the antibody on vessel length as shown in FIG. 16a;

FIG. 16b (top right) illustrates a graph summarising the effect of the antibody on vessel number as shown in FIG. 16a;

FIG. 16b (bottom) illustrates a graph summarising the effect of the antibody on maximum vessel length as shown in FIG. 16a;

FIGS. 17a(1) and a(2) illustrates photographs of sections of aorta cultured in the presence of a control antibody and anti Cathepsin S antibody 1E11 at 1 ug/ml, 5 ug/ml, 10 ug/ml, and 100 ug/ml, 1 ug/ml concentrations at ×4 and ×20 magnification respectively.

FIG. 17b illustrates a graph summarising the effect of the antibody in the experiment illustrated in FIG. 17a on number of tubules, mean tubule length and maximum tubule length.

FIG. 18 illustrates the amino acid sequence of the $V_H$ and $V_L$ chains (SEQ ID NO:7 and SEQ ID NO:6, respectively) of the 1E11 inhibitory antibody, with CDRs highlighted in bold and underlined, as determined from DNA sequencing of the VH and VL regions.

MATERIALS AND METHODS

Cell Lines and Culture Conditions

Figure 1:
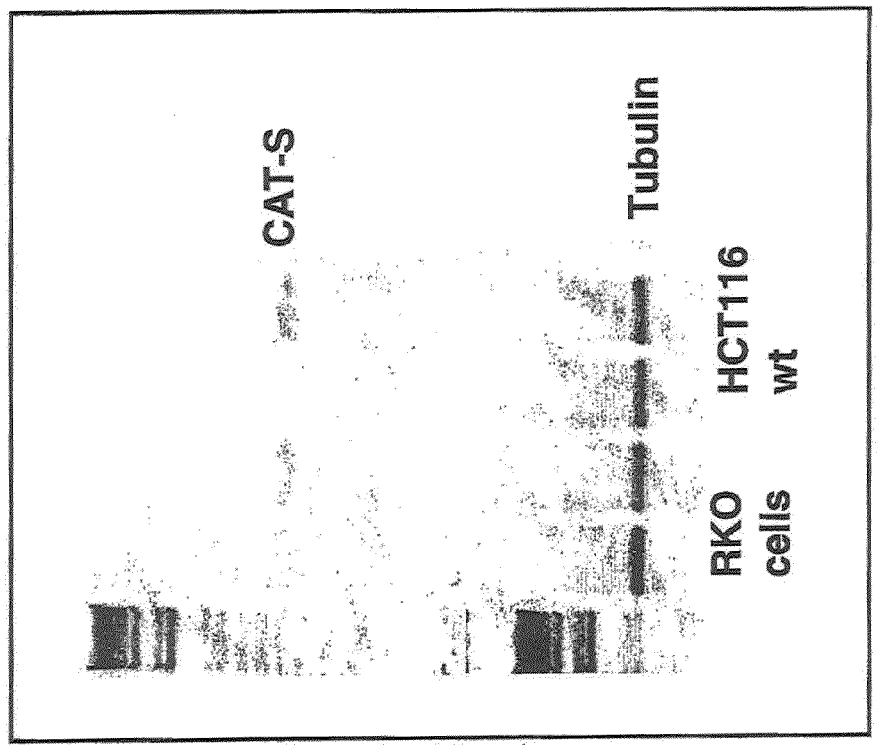
FIG. 1 illustrates analysis of CatS RNA expression in HCT116 cells and RKO cells, with/without a 48 hour CPT11 treatment.

The HCT116 (p53 wild type) human colorectal adenocarcinoma cell line was maintained in McCoys medium (Invitrogen, UK). The RKO (p53 will type), H630 (p53 mutant) and HT29 (p53 mutant) colorectal adenocarcinoma cell lines were maintained in Dulbecco's Modified Eagle's Medium (DMEM, Invitrogen, UK). All medium was supplemented with 10% FCS, 1% pen/strep, 1% L-Glutamine (All Invitrogen, UK).

Treatment of Cell Lines with Chemotherapeutic Agents

Cells in a log phase of growth were seeded into 6 well tissue culture plates at ~20% confluence and incubated overnight to allow adherence to the plate. Wells were treated with CPT11 (Irinotecan) and 5-Fu (Fluorouracil) at varying concentrations (including 7.5 µM) for 48 hours. Chemotherapy was substituted with saline in control wells.

Western Blotting

Cells were washed in PBS (5 minute centrifugation at 1500 rpm) prior to lysis with RIPA buffer containing a protease inhibitor cocktail (Calbiochem, UK) as previously described. Whole cell lysates were loaded onto 12% SDS-PAGE gels at equal concentrations. Gels were run overnight at 50V prior to semi-dry transfer onto nitrocellulose membrane at 20V for 45 minutes (BioRad, UK). The nitrocellulose membrane was blocked using PBS (3% Milk powder) for ~1 hour, and washed ×3 with PBS (0.01% tween) for 5 minutes. The membrane was then probed with a 1 in 1000 dilution of CatS Mab (1E4 Mab or 1E11 Mab) in PBS (3% Milk powder) for 1 hour. The membrane was washed ×3 with PBS (0.01% tween) for 5 minutes prior to the addition of a 1 in 5000 dilution of secondary goat anti mouse-HRP conjugated antibody (BioRad, UK) in PBS (3% Milk powder) for 1 hour. This was then washed three times in PBS (0.01% tween) for 5 minutes each. The membrane was 'developed' by ECL (enhanced chemiluminescence) using the Super Signal kit (Pierce). The membrane was incubated in ECL solution for 5 minutes, prior to exposure to photographic film for various time periods. The photographic film was washed in developer solution (Sigma, UK) for 1 minute, rinsed with water, and washed in fixer solution (Sigma, UK) again for 1 minute before being rinsed and dried.

Flow Cytometry

Cells were collected from tissue culture plates using a scraper and washed ×3 in PBS (0.01% tween) (5 minute centrifugation at 1500 rpm). Approximately $5 \times 10^5$ cells were placed in appropriately labelled tubes. Cells were incubated with 50 µl anti-CatS or Isotype control (Sigma, UK) for 1 hour at room temperature. Following incubation each tube was washed ×3 in PBS (0.01% tween) (5 minute centrifugation at 1500 rpm). Samples were then incubated with a 1 in 15 dilution of FITC-conjugated goat anti-mouse secondary antibody (Sigma, UK) (samples kept in dark at room temperature). Following incubation each tube was washed ×3 in PBS (0.01% tween) (5 minute centrifugation at 1500 rpm). Samples were resuspended in 0.5 ml of PBS prior to immediate analysis using the Cyan flow cytometer (Dako, UK).

RT-PCR

RT-PCR was performed using a PTC 225 Gradient Cycler (MJ Research Incorporated). RNA was collected using the RNA STAT-60 reagent (Tel-Test Friendswood, USA) according to the manufacturers instructions and cDNA synthesised using 1 ug RNA and a reverse transcriptase kit (GIBCO Invitrogen, Paisley, UK). The primer sets used for RT-PCR were CatS forward primer 5'-ACT CAG AAT GTG AAT CAT GGT G-3' (SEQ ID NO:9) and CatS reverse primer 5'-TTC TTG CCA TCC GAA TAT ATC C-3' (SEQ ID NO:10) and Beta 3 integrin primer 5'-CCTACATGACCGAAAATACCT-3' (SEQ ID NO:11) and 5'-AATCCCTCCCCA-CAAATACTG-3' (SEQ ID NO:12) Gene expression was analysed using a biomix PCR mixture (Bioline, UK) containing 25 ul Biomix; 1.5 µl forward primer; 1.5 µl reverse primer; 2 µl cDNA; 20 µl $dH_2O$. PCR conditions consisted of an initial denaturation step of 95 C for 10 minutes, followed by either 32 or 45 cycles of 95° C. for 30 sec; 55° C. for 30 sec; 72° C. for 90 sec, with a final extension of 72° C. for 10 minutes. 5 µl of amplified product from the 32 and 45 cycle reactions was loaded onto a 1.5% agarose gel (0.001% ethidium bromide) which was run at 90V for 40 minutes prior to analysis on a UV box.

Xenograft Models 6-8 week old female SCID mice were implanted with $2 \times 10^6$ HCT116+/+ human colorectal adenocarcinoma cells into each flank. HCT116 cells in a log phase of growth were harvested, washed in PBS and resuspended in HBSS. They were mixed with equal volumes of matrigel to give a final concentration of $5 \times 10^6$ cells/ml. Mice were randomly separated into treatment groups on day 5 after implantation and treated with various regimes of CatS Mab or Isotype control Mab (10 mg/kg) with/without 5Fu (15 mg/kg daily or 70 mg/kg twice weekly). All drugs were administered through a bolus injection. Animals were sacrificed at various time points and tumours were removed for analysis.

Immunohistochemistry

Paraffin embedding of formalin-fixed xenograft/organ tissue samples, section cutting and H&E (haematoxylin and eosin) staining of tissue sections were performed as previously described. Immunostaining was performed using the avidin-horseradish peroxidase method (Vectorlabs ABC Kit).

Briefly, sections were deparaffinised by passing from xylene to alcohol to running water. Endogenous peroxidase activity was blocked by incubation in 3% $H_2O_2$ in methanol for 10 min. Sections were then boiled in citrate buffer, pH6.0, for 22 min. Incubation in 5% normal horse serum blocking solution was carried out for 20 min at room temp. Sections were incubated with primary antibody at 4° C. overnight. Appropriate isotype controls were used at the same dilutions as primary antibodies.

For peroxidase staining, sections were incubated with biotinylated pan-specific secondary antibody (Vector Laboratories) for 30 min at room temp followed by incubation with the Vectastain Elite ABC reagent (Vector Laboratories) for a further 30 min at room temp. For visualisation sections were stained with 3,3'-diaminobenzidine and counterstained with Gill's II hematoxylin solution. Staining using the cleaved caspase-3 polyclonal antibody (Cell Signalling Technology) was carried out according to the manufacturer's instructions. For detection of antibody localisation, after prior administration to xenograft models, no primary antibody incubation step was required.

AccuMax™ Array slides were stained according to the manufacturers instructions using a 1:100 dilution of CatS monoclonal antibody and a secondary biotinylated horse antibody (Vector Laboratories, CA). Slides were counter stained with haematoxylin prior to mounting and analysis.

Confocal Microscopy

HCT116 cells were stained for CatS expression using a CatS monoclonal antibody as before. Cells were grown on glass coverslips, fixed using ice-cold acetone and incubated with CatS antibody at a 1:100 dilution. Coverslips were rinsed with PBS and incubated with antimouse AlexaFluor® 488 labelled secondary antibody. Coverslips were washed again using PBS, mounted using PermaFluor mounting media and visualised by confocal microscopy.

Capillary-Like Tube Formation Assay

The effect of the CatS mAb on endothelial cell tube formation was assessed as follows. Two hundred microliter of Matrigel (10 mg/ml) was applied to pre-cooled 48-well plates, incubated for 10 min at 4° C. and then allowed to polymerize for 1 h at 37° C. Cells were suspended in endothelial growth cell medium MV (Promocell), containing 200 nM of the appropriate antibody. Five hundred microliter ($1 \times 10^5$ cells) were added to each well. As controls, cells were incubated with vehicle-only control medium containing the appropriate volumes of PBS. After 24 h incubation at 37° C. and 5% CO2, cells were viewed using a Nikon Eclipse TE300 microscope.

Cell Viability and Proliferation Assays

Cytotoxic and proliferative effects of the CatS monoclonal antibody on U251mg astrocytoma cells can be tested as previously described. Briefly, cells are added to a final concentration of $1 \times 10^4$ cells/200 μl per well of a 96-well microtiter plate (Corning Costar). Appropriate concentrations of monoclonal antibody (100 nM) or vehicle-only control media are added. Plates are incubated at 37° C. and 5% $CO_2$ for 24, 48, 72 and 96 hrs respectively. After incubation, 10 μl of 10 mg/ml MTT is added and incubated for a further 2 h at 37° C. and 5% $CO_2$. The medium is carefully removed and formazan crystals dissolved in 100 μl/well of DMSO. Absorbance is measured as described above and the results expressed as the percentage of cell viability and proliferation relative to each vehicle-only control. All tests are performed in quadruplicate.

Wound Assay

The in vitro migration assay used in these studies is a modified version of the method described by Ashton et al (1999). HMEC-1 is plated into individual chambers on a glass slide and grown to 90% confluence overnight. The medium is removed and the monolayer wounded. The monolayer is re-supplemented with fresh medium and the required volume of antibodies added to give the required final concentration.

Slides are removed at fixed time points until complete closure of the wound, then fixed in 4% PBS buffered paraformaldehyde. The extent of "wound" closure is blindly assessed microscopically by an independent investigator and quantified using a calibrated eyepiece graticule (1 mm/100 μm graduation) at 20× magnification (Olympus BX 50). The extent of closure in the antibody treated slides is compared to time matched sham treated controls and the % inhibition of wound closure compared to time matched controls calculated.

Rat Aorta Model

Male Wistar rats are euthanised and the thoracic aorta is aseptically removed and sectioned into 1 cm thick rings. The rings are washed ten times in sterile medium to remove any bacteria and embedded into Matrigel on 24 well plates. The wells are supplemented with 2 ml of medium and increasing concentrations of antibodies. The plate is incubated for 8 days and post incubation the Matrigel and rings are fixed in 4% PBS buffered paraformaldehyde and stored in PBS. The extent of vessel development is blindly assessed microscopically by an independent investigator and quantified using a calibrated eyepiece graticule (1 mm/100 μm graduation) at 20× magnification (Olympus BX 50). The extent of vessel length, maximum vessel length and number of vessels in each field of view is measured and compared to time matched sham controls and the % inhibition calculated.

Sponge Assay

Polyether sponges are subcutaneously implanted in C57 black mice and injected on alternate days with 10 ng bFGF or 10 ng bFGF+ antibodies. After 14 days of treatment, sponges are harvested, sectioned and stained with H&E (A).

Oxygen-Induced Retinopathy (OIR) Neonatal Mouse Model

The animal model of oxygen-induced retinopathy employed in this investigation is that described by Smith et al and now widely used for studies testing anti-angiogenic therapies for retinal neovascularisation (Smith et al., 1994). Litters of postnatal mice and their nursing dams are placed in 75% oxygen at postnatal day 7 (P7) and returned to room air at P12. During the 5-day period of hyperoxia the central retinal capillary beds undergo vascular regression and halted development. Upon return to room air the central retina becomes measurably hypoxic with an associated increase in vasogenic growth factors of the VEGF family. An aggressive neovascular response ensues with extra-retinal new vessels developing by P15. Neovascularization is maximal at P17 and regresses after P21.

Unfixed neural retina are dissected and subjected to ultrasonic disruption in RIPA buffer. For quantification of HP-protein binding, retinal samples from P13 and P17 mice are prepared for a HP competitive enzyme-linked immunosorbent assay (ELISA) methodology. Briefly, 100 µl of sample or standard in duplicate are serially diluted in PBS/5% Tween 20 in a 96-well polystyrene assay plate (Corning Inc., Corning, N.Y.) and incubated with 25 µl of rabbit polyclonal antibody against HP (1:3300 in PBS/5% Tween) for 1 hour at 37° C. The contents of each well is then transferred to NUNC C96 Maxisorp plates that are precoated with solid phase antigen (1:5000 in carbonate buffer, pH 9.6) overnight at 4° C. and blocked with 1% gelatin for 1 hour. The competition between solid phase and soluble antigens proceeds for 1 hour at 37° C., after which the wells are washed 4×5 minutes with PBS/5% Tween, and 100 µl of 1:2000 alkaline-phosphatase goat anti-rabbit IgG (Sigma-Aldrich) is added to each well. Plates are then washed 4×5 minutes with PBS/5% Tween, and 100 µl of 1 mg/ml of the alkaline-phosphatase substrate, 4-nitrophenyl phosphate disodium salt hexahydrate (Sigma-Aldrich) dissolved in 10% diethanolamine buffer (pH 9.6) is added to each well. The color development of the subsequent reaction is measured at 405 nm every 5 minutes for 2 hours on a Safire microplate reader (Tecan Instruments) and reaction kinetics analyzed using Magellan 3 software. Sample HP-1 binding is determined by comparison to a Lineweaver-Burk enzyme kinetic standard curve, and is expressed as a proportion of sample protein concentration. The solid-phase antigen used in the assay is HP, which is reductively bound to bovine serum albumin. Statistical analysis is conducted using the Student's t-test and a P value _0.05 is considered significant.

Results

This study investigated the expression of CatS on colorectal cancer cell lines and the ability of chemotherapy to induce CatS expression. It further examined the effects of an Anti CatS specific monoclonal antibody on tumour development and viability both In Vitro and In Vivo.

Examples 1 to 3

CatS expression was examined at the mRNA, protein and cell surface levels.

Example 1

RT semi quantitative PCR was used to examine mRNA levels of CatS in four colorectal cell lines (HCT116+/+, RKO+/+, H630 p53 mutant and HT29 p53 mutant) with/without 7.5 µM CPT11 treatment. RNA levels were analysed following 32 and 45 cycle of PCR to determine relative differences in expression between treated and untreated samples. All four cell lines displayed basal expression of CatS while both the HCT116+/+ and RKO+/+ cell lines showed an increase in expression in response to chemotherapy as shown in FIG. 1.

Example 2

Figure 2:
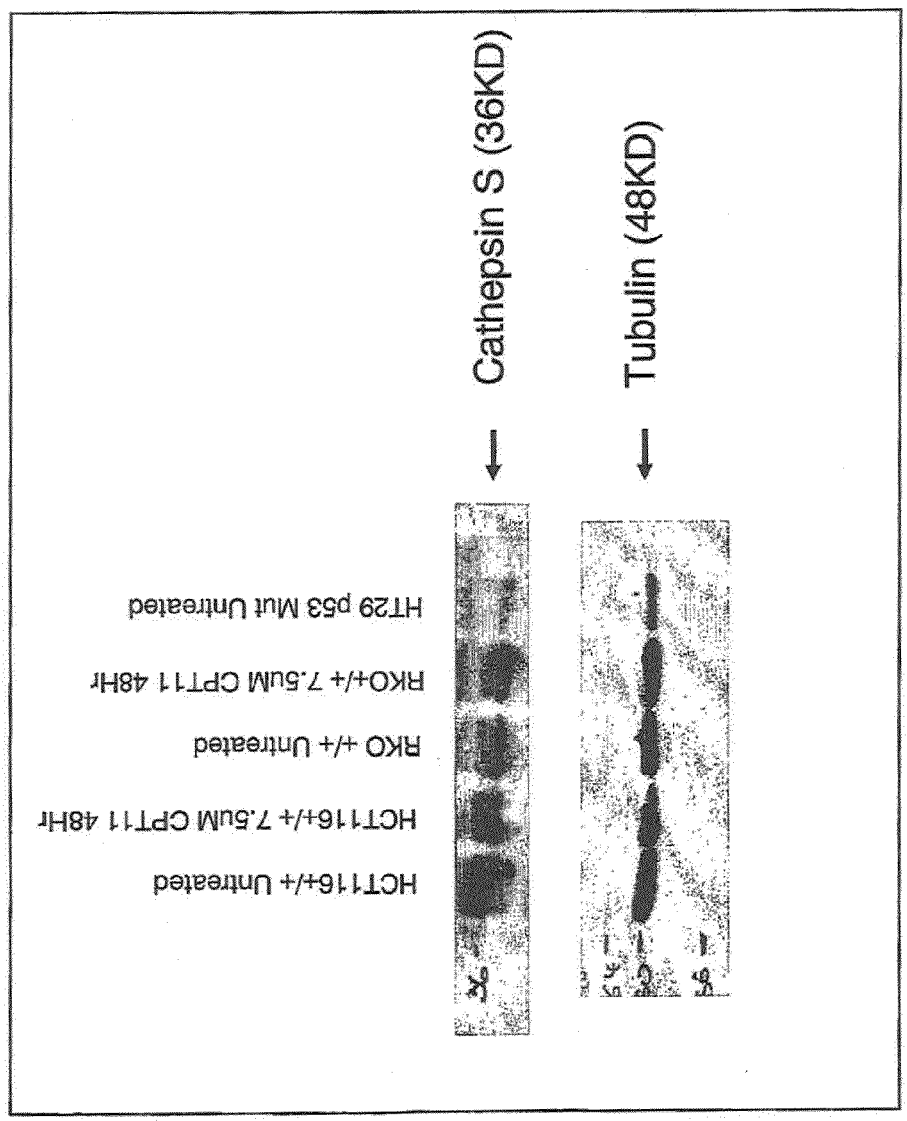
FIG. 2 illustrates Western blot analysis of CatS and gamma tubulin protein expression in HCT116+/+ cells, RKO+/+ cells and HT29 p53 mutant cells with/without a 48 hour CPT11 treatment.

CatS expression was examined at the protein level by performing western blot analysis on whole cell lysate preparations made from three cell lines (HCT116+/+, RKO+/+ and HT29). Whole cell lysates were prepared on samples with/without 48 hour CPT11 treatment (7.5 µM) for both the HCT116+/+ and RKO+/+ cell lines. All three cell lines showed positive expression of CatS (FIG. 2) with no obvious difference in whole protein expression levels evident between the treated and untreated HCT116+/+ or RKO+/+ samples.

Example 3

Figure 3:
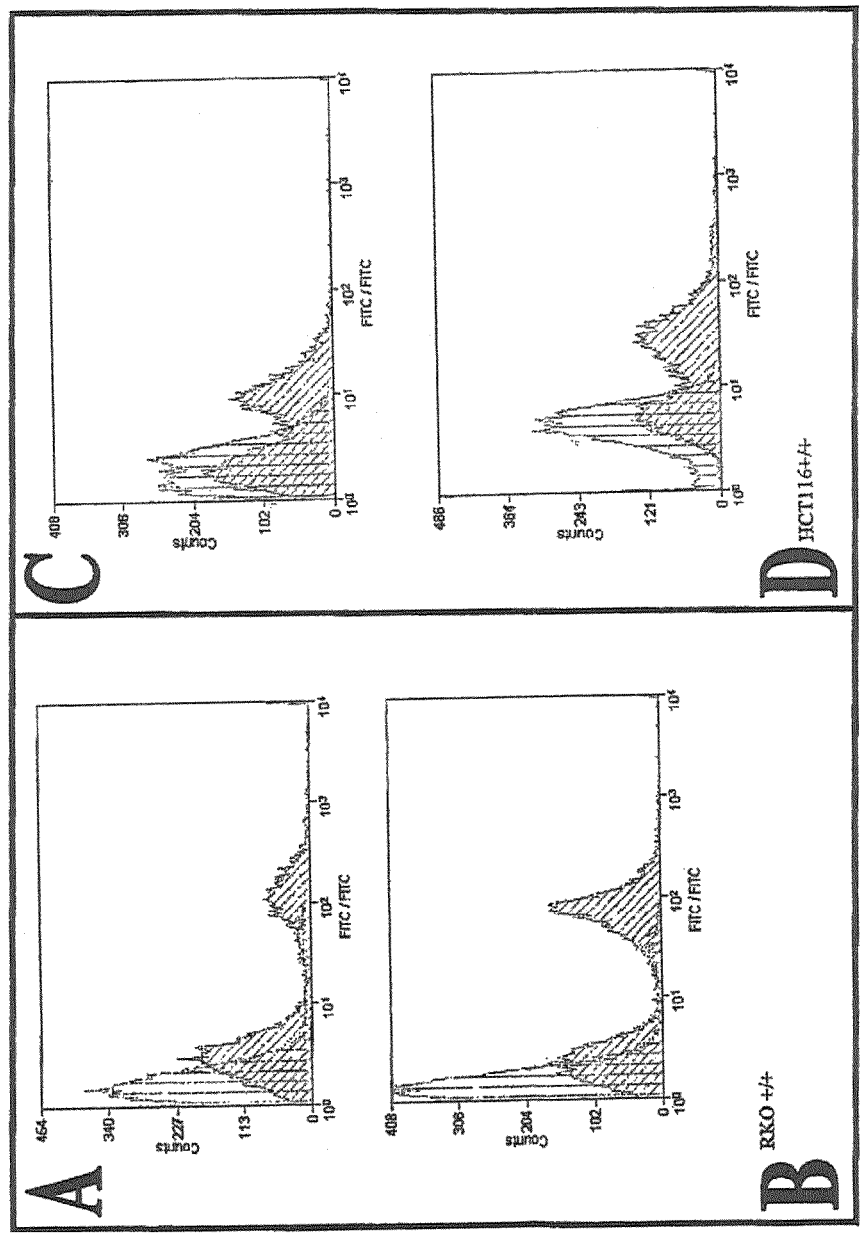
FIG. 3 illustrates flow cytometric analysis of CatS cell surface expression on RKO+/+ cells untreated (3A) and CPT11 48 hour treated (3B) and HCT116+/+ cells untreated (3C) and CPT111 48 hour treated (3D). Cells were stained with CatS monoclonal antibody (Green—lower peaks on each graph (diagonal stripes)) and Isotype matched control (Red—high peak on left on each graph (vertical stripes)).
Figure 4:
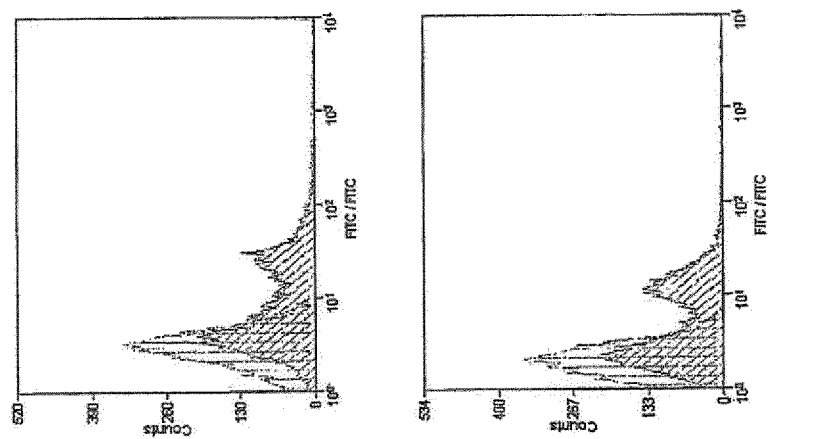
FIG. 4 illustrates flow cytometric analysis of CatS cell surface expression on H630 cells untreated (4A) and CPT11 48 hour treated (4B). Cells were stained with CatS monoclonal antibody (Green—double peak on each graph (diagonal stripes)) and Isotype matched control (Red—single higher peak on left of each graph (vertical stripes)).

Cell surface expression of CatS was examined using flow Cytometry. HCT116+/+, RKO+/+, and H630 p53 mutant cells were analysed for cell surface expression with/without CPT11 treatment. The RKO+/+ cell line showed 38% positive basal cell surface expression which was increased to 49% following chemotherapy induction (FIG. 3 A-B). The HCT116+/+ cell line showed 39% positive basal cell surface expression which was increased to 59% following chemotherapy induction (FIG. 3 C-D). The H630 p53 mutant cell line showed 37% positive basal cell surface expression which was increased to 41% following chemotherapy induction (FIG. 4 A-B).

Example 4

Figure 5:
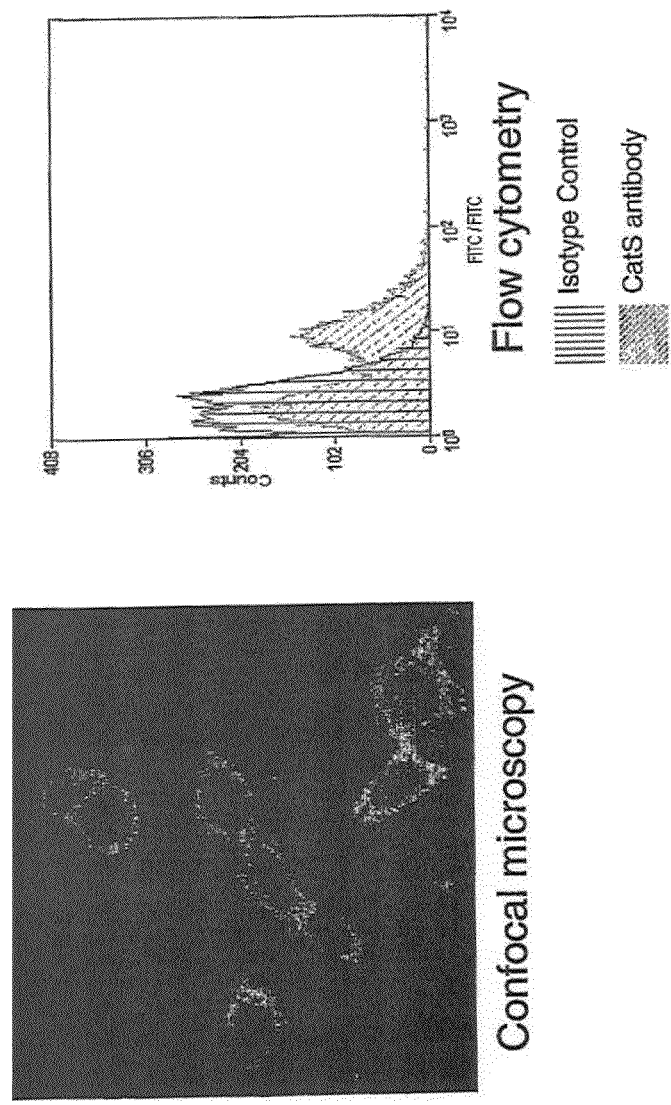
FIG. 5 illustrates a photograph showing the results of immunocytochemical analysis using the 1E11 CatS monoclonal antibody, revealing that CatS expression is localised to the cell surface on HCT116 cells The right panel shows the results of flow cytometry analysis, where a 38% increase in fluorescent intensity was observed in HCT116 cells stained for CatS in comparison to the isotype control

The presence of Cathepsin S on the cell surface of tumour cells was further confirmed using confocal microscopy. HCT116 cells were stained for CatS expression using a CatS monoclonal antibody as before. The results are shown in FIG. 5. Immunocytochemical analysis using the 1E11 CatS monoclonal antibody, revealed that CatS expression is localised to the cell surface on HCT116 cells, which was also confirmed by flow cytometry analysis, where a 38% increase in fluorescent intensity was observed in HCT116 cells stained for CatS in comparison to the isotype control Example 5

Figure 6:
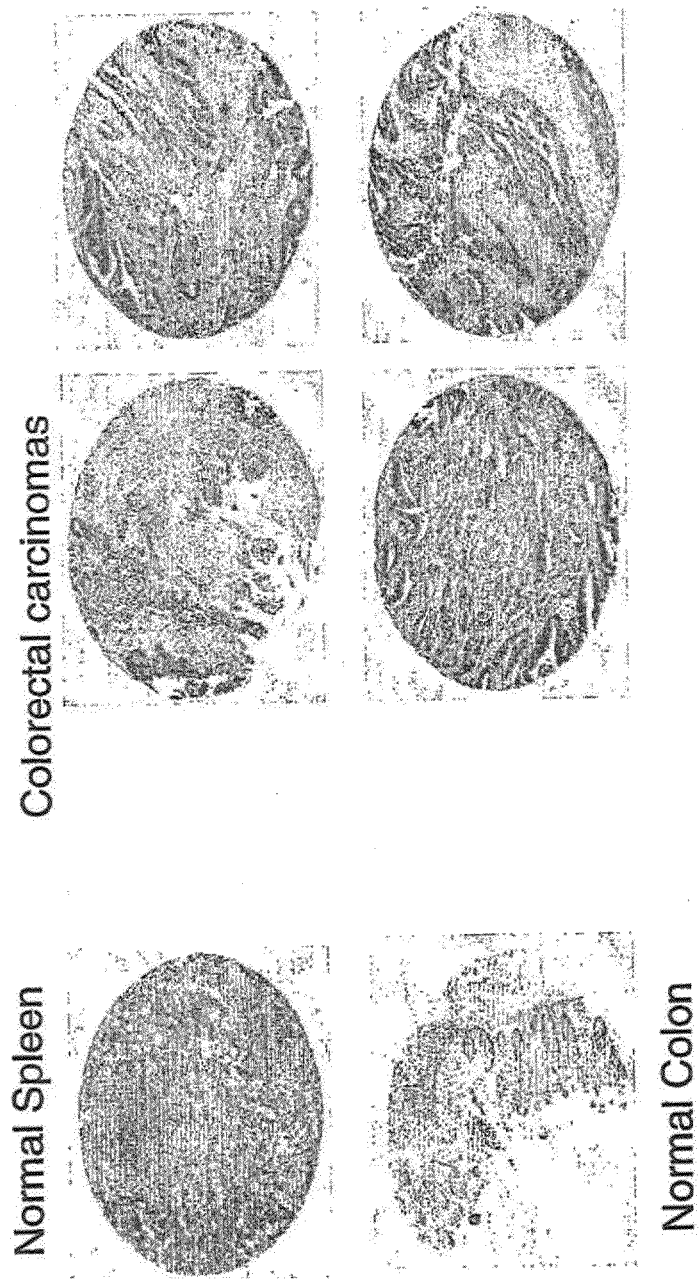
FIG. 6 illustrates the results of immunohistochemical detection of CatS expression in colorectal carcinoma biopsies And in normal spleen and colon samples.

In contrast, normal sections of colon do not show the expression of Cathepsin S on the cell surface as demonstrated for colorectal carcinomas. FIG. 6 shows the results of immunohistochemical detection of CatS expression in colorectal carcinoma biopsies. Tissue sections were stained for CatS expression using a monoclonal antibody raised against the mature human CatS protease. Staining of normal sections of human colon demonstrated little or no staining for CatS, whereas colorectal carcinoma biopsy sections had dense staining for CatS.

Example 6

It has been reported that Cathepsin S co-localises with integrin αvβ3 as a receptor on the vascular smooth muscle cell surface in atherosclerosis and restenosis after angioplasty (Cheng et al, Am J Pathology, 2006, 168: 685-694).

Figure 7:
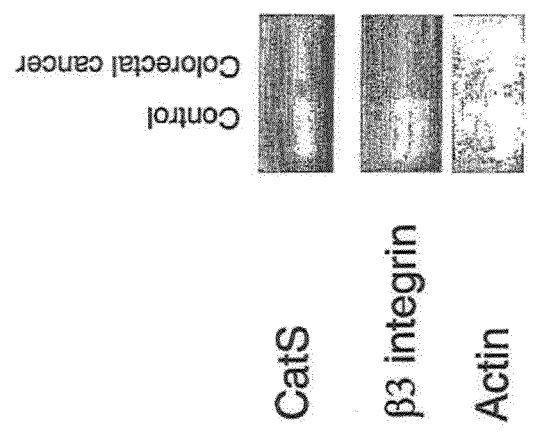
FIG. 7 illustrates analysis of CatS and β integrin RNA expression in HCT116+/+, colorectal cancer cells compared to control (non-tumor cells). RNA levels were analysed following 35 cycle of PCR.

The present inventors investigated whether the localisation of Cathepsin S on the surface of tumour cells demonstrated herein was associated with such integrins. As shown, in FIG. 7, which shows the results of analysis of CatS and β3 integrin RNA expression in HCT116+/+, colorectal cancer cells. following 35 cycles of PCR, although Cathepsin S is strongly expressed, no β3 integrin RNA expression was demonstrated, showing that the localisation of Cathepsin S on the cell surface of tumour cells is unrelated to its expression in vascular smooth muscle cells under conditions of atherosclerosis.

Example 7

Studies were then carried out on the effect of combination therapy using the chemotherapeutic agent 5Fu and the Cathepsin S inhibitory antibody 1E11 (also referred to herein as CatS Mab).

As shown in co-pending PCT application WO2006/109045, the contents of which are incorporated herein by reference, which claims priority from GB0507219.4 and GB0507272.3, this antibody has potent inhibitory activity. In a fluorimetric assay using the fluorigenic substrate, the antibody inhibits the proteolytic activity of CatS. Further the antibody has also been shown to potently inhibit tumour cell invasion in invasion assays using the PC3 prostate carcinoma cell line, the U251mg astrocytoma cell line, the HCT116 colorectal carcinoma cell line, the MDMB231 breast cancer cell line and the MCF 7 breast cancer cell line. Furthermore, antiangiogenesis effects of this antibody have been demonstrated in a Matrigel assay, in which the antibody was shown to inhibit capillary tubule formation (see later).

Figure 8A:
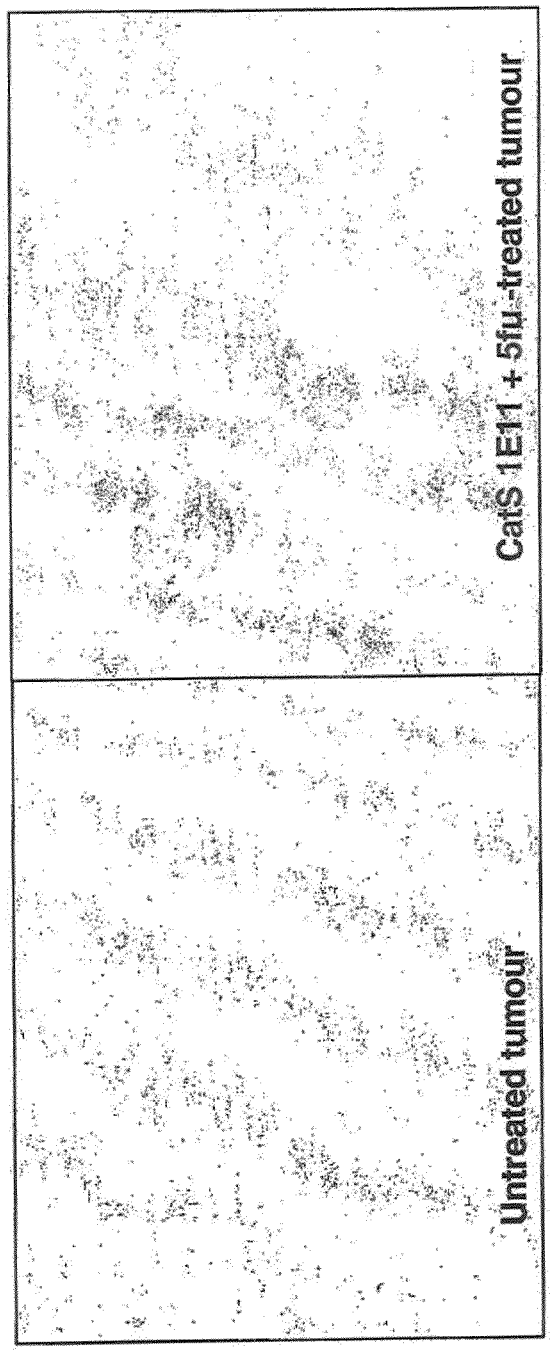
FIG. 8a illustrates immunohistochemical detection of CatS 1E11 mAb localisation to tumor in untreated and treated (CatS 1E11+5Fu (IC50)) xenograft models. Dark (Brown) staining indicates positive staining.
Figure 8B:
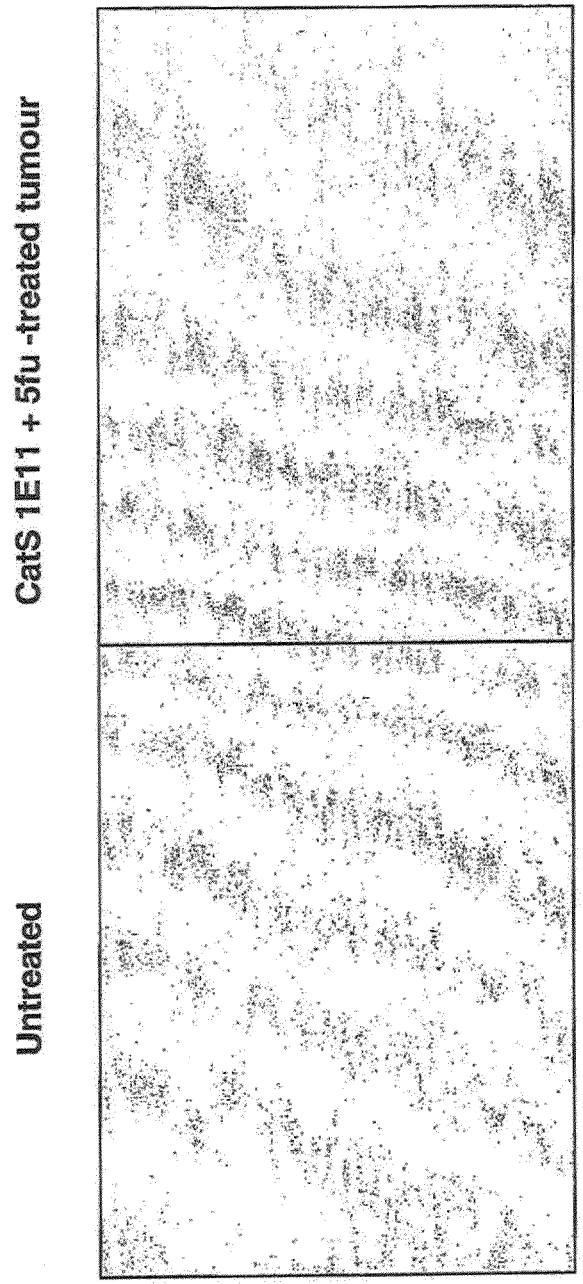
FIG. 8b illustrates immunohistochemical detection of CatS 1E11 mAb localisation to tumor in untreated and treated (CatS 1E11+5Fu (IC50)) xenograft models. Dark (Brown) staining indicates positive localisation.

Studies into in vivo expression of CatS were carried out in Xenograft models of colorectal cancer. Models were treated with the chemotherapeutic agents 5Fu, CPT-11 and oxaliplatin (15 mg/kg-70 mg/kg doses) alone or in combination with 10 mg/kg 1E11 CatS monoclonal antibody. Paraffin embedded tissue sections were examined for antibody localisation following treatment. Tumour samples obtained from animals treated with CatS Mab in combination with 5-Fu stained positive for IgG (FIGS. 8a and 8b) showing that the CatS Mab can be successfully directed to the positively expressing tumour cells.

Example 8

Figure 9:
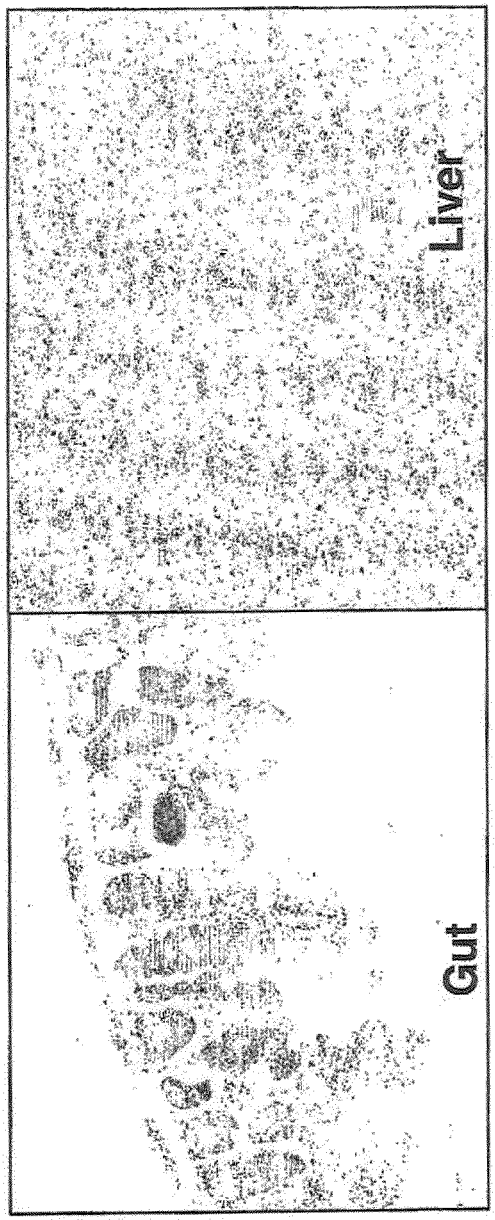
FIG. 9 shows photographs of gut and liver sections after nine-day drug regime (CatS 1E11+5Fu (IC50)) in xenograft model organs.

All major mouse organs were examined for architectural changes following treatment. No signs of pathological change were seen. FIG. 9 shows photographs of gut and liver sections after nine-day drug regime (CatS 1E11+5Fu (IC50)) in xenograft model organs. The in vivo studies suggest that repeated treatment with 10 mg/kg of 1E11 Mab in combination with chemotherapy has no adverse toxic effect (FIG. 9).

Example 9

Figure 10:
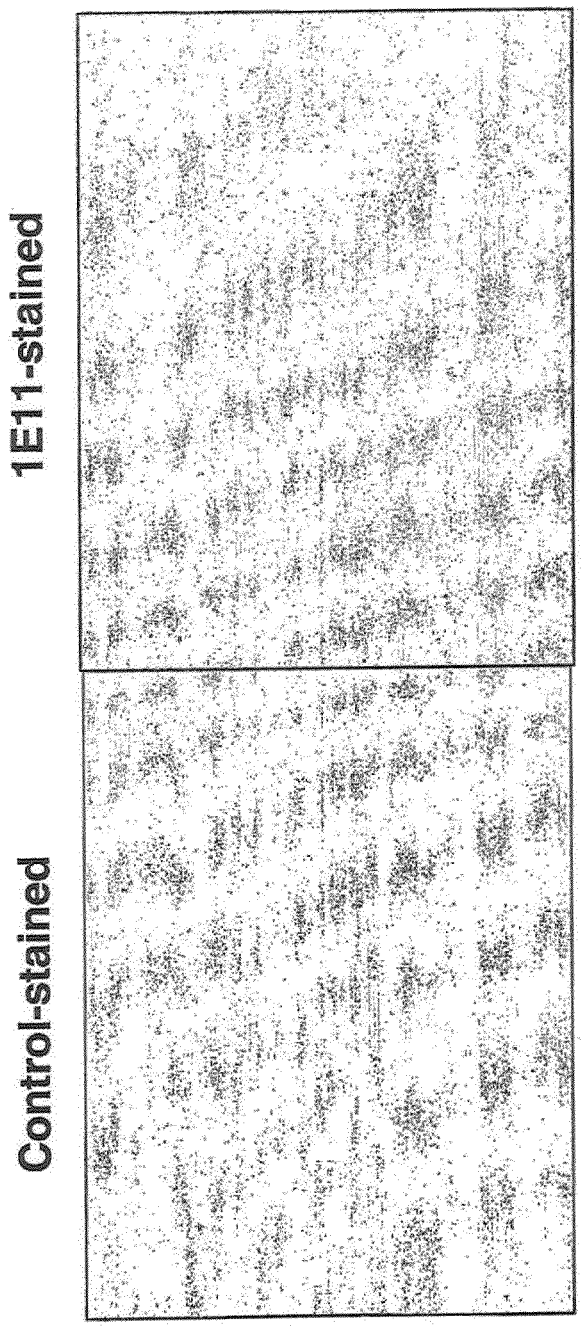
FIG. 10 illustrates immunohistochemical detection of CatS expression in 5-Fu-treated tumor sections. Sections were stained with Mouse IgG1 isotype control or CatS 1E11 MAb.
Figure 11:
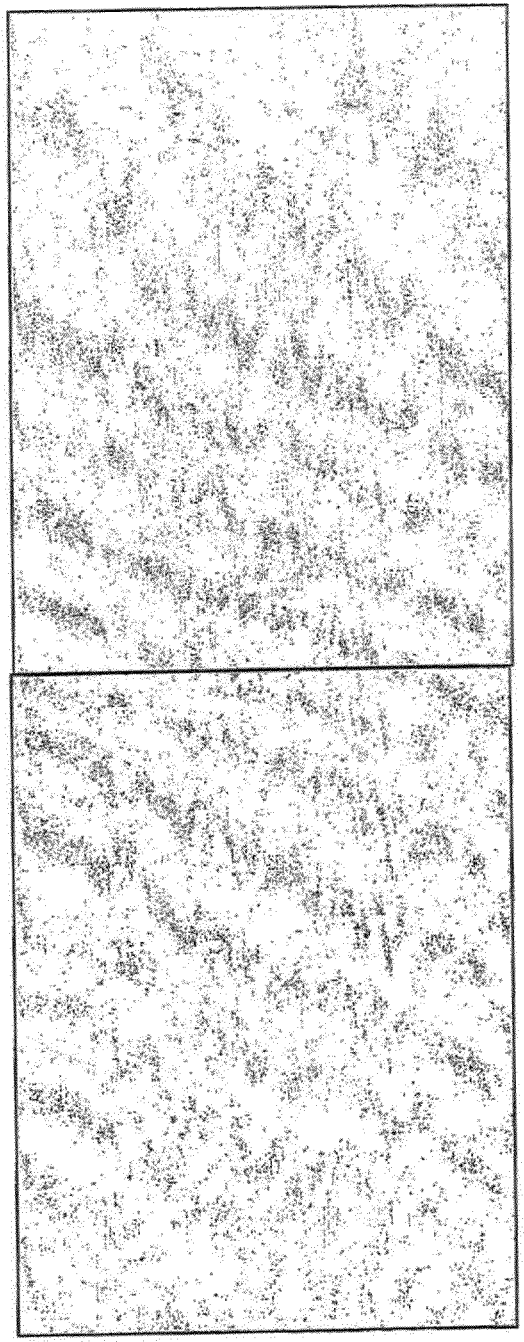
FIG. 11 illustrates immunohistochemical detection of CatS expression in untreated and 5-Fu-treated (15 mg/kg) tumor sections. Sections were stained with CatS 1E11 mAb.
Figure 12:
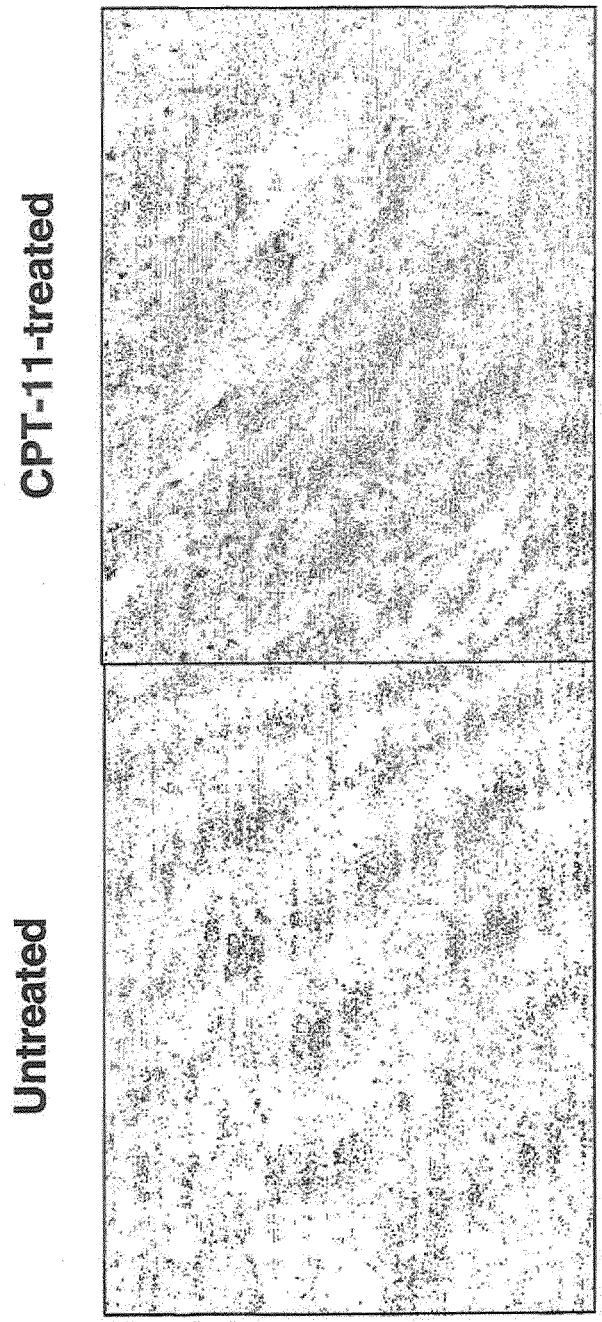
FIG. 12 illustrates immuhohistochemical detection of CatS expression in untreated and CPT-11-treated (15 mg/kg) tumor sections. Sections were stained with CatS 1E11 mAb.
Figure 13:
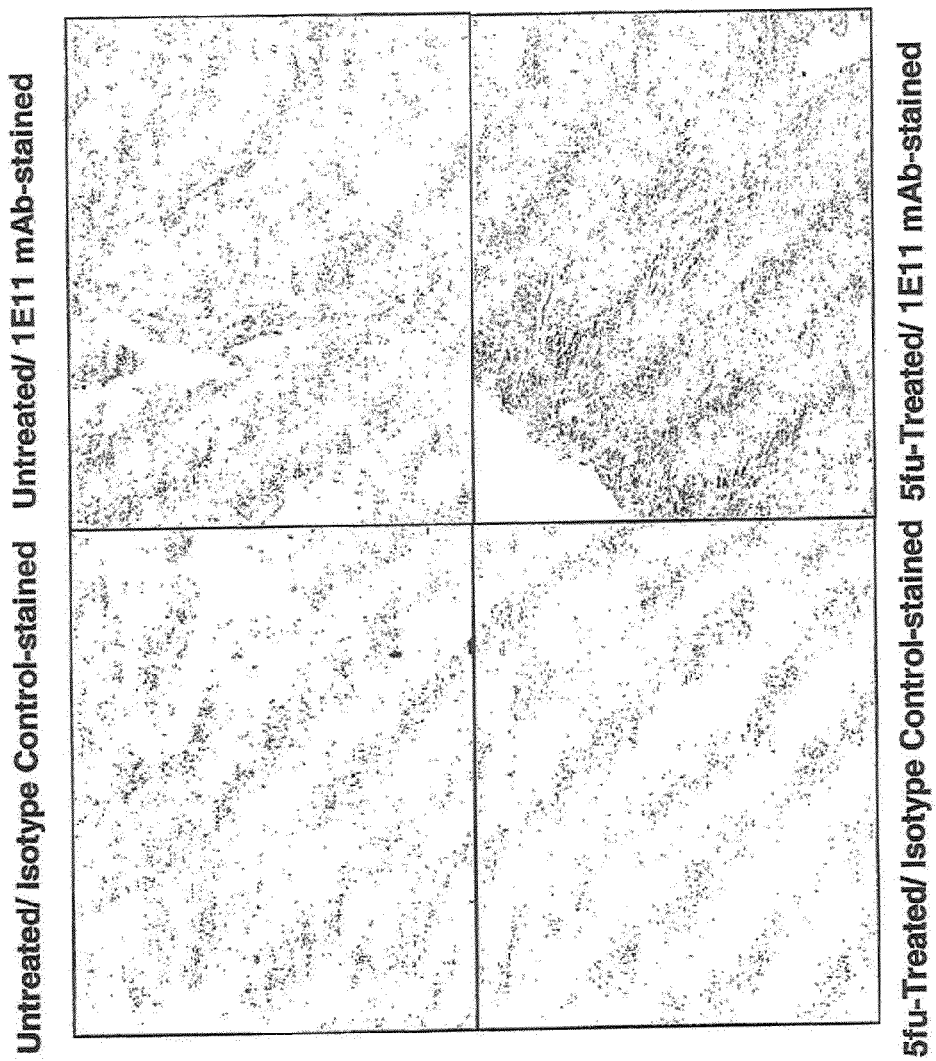
FIG. 13 illustrates immunohistochemical detection of CatS expression in untreated and 5-Fu-treated tumor sections. Sections were stained with Mouse IgG Isotype control (R&D Systems) or CatS 1E11 mAb.

Tumour sections were stained using the 1E11 mAb to detect CatS expression (FIG. 10). A mouse IgG isotype was used as a control. FIGS. 11 and 13 show that, in tumour sections obtained from mice treated with 5-Fu an upregulation in CatS expression was observed with FIG. 12 showing a similar result in sections obtained from mice treated with CPT-11.

Example 10

Figure 14:
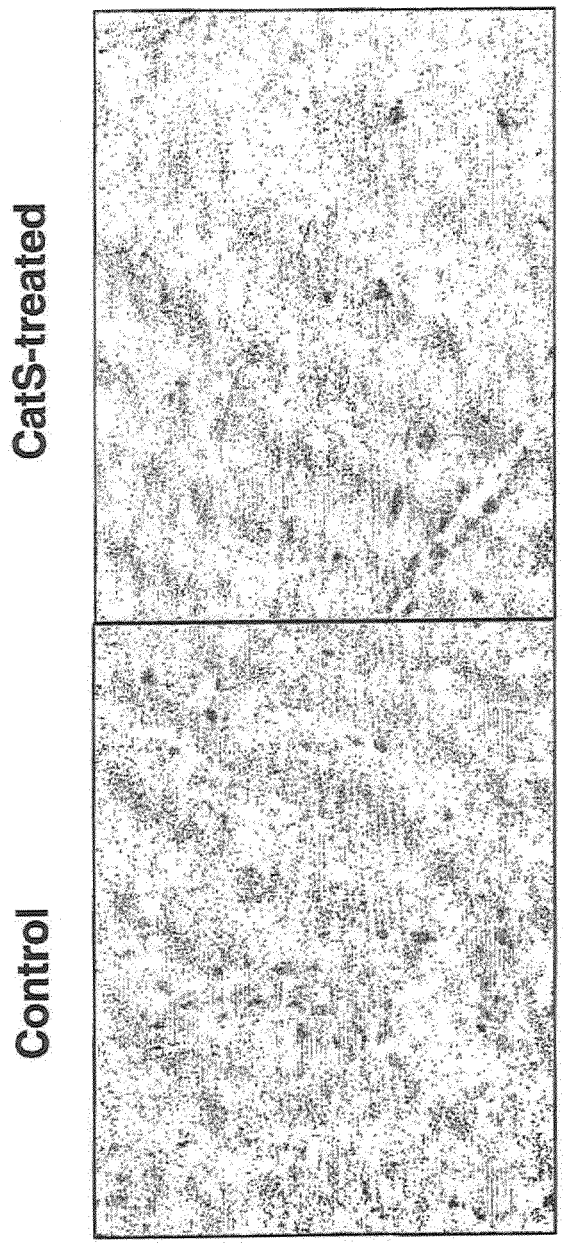
FIG. 14 illustrates apoptosis Detection in control (Mouse IgG1+5-Fu) and treated (CatS 1E11+5Fu (IC50) tumor sections. Sections were stained with anti-cleaved caspase-3 (Cell Signalling Technology).

The effect of combination treatment on tumour tissue was examined using an anti-cleaved caspase-3 polyclonal antibody (FIG. 14). An increase in caspase 3 activity was observed in treated tissue indicating that the CatS Mab is having an influence on apoptosis.

Example 11

CatS Antibodies can Inhibit Tube-Like Formation in Human Endothelial Cells

Using the Matrigel morphogenesis assay described by Grant et al (Cell 1989 Sep. 8; 58 (5): 933-43), capillary-tubule formation assays were performed with human microvascular endothelial cells (HMECs) cultured on Matrigel enabling the endothelial cells form tube-like structures, with invasive sprouts extending from individual cells to form contacts with nearby endothelial cells. FIG. 15a illustrates the results when the HMEC cells were cultured in the presence of two CatS antibodies (1E11 and 1E4) or isotype control. Extensive tube-like structures are evident in the vehicle-only control and isotype control antibody (200 nM) panels; however this tube formation is almost completely abolished in the presence of either of the 1E11 (mAb1) or 1E4 (mAb2) antibodies (200 nM). These results were then quantified as shown in FIG. 15b, which illustrates the inhibition of capillary cell branching observed in the presence of 1E11 (upper panel) or 1E4 (lower panel).

Both antibodies have been previously shown to bind specifically to CatS with no cross-reactivity with other cathepsins, in particular those with the greatest homology to CatS. Antibodies 1E11 and 1E4 have both been characterised for their ability to inhibit the catalytic activity of CatS; 1E11 can specifically inhibit the activity of CatS whereas 1E4 has no discernable effect. Therefore, the results from the capillary-tube assay show that the sequestering of active CatS secreted from the endothelial cells by either an inhibitory or non-inhibitory CatS mAb is sufficient to prevent the migration and arrangement of the endothelial cells into tube-like structures. The F47 Cathepsin S 1C11 1E11 1E4 cell line which is the hybridoma cell line that produces the IE4 antibody has been deposited with the European Collection of Cell Cultures ("ECACC") under Accession No. 15072905.

Example 12

CatS Antibodies can Inhibit Tube Like Formation in Rat Aortic Arch Ex Vivo Model To evaluate further the role of CatS in angiogenesis, an ex vivo rat aortic arch assay was performed. Sections of the aorta (1 mm) were cultured within a thin layer of Matrigel in the presence of the inhibitory antibody and appropriate controls. The formation of tube-like vessels from the aorta were monitored and quantified after 7 days by measuring the reduction in the number of vessels, mean vessel length and maximum vessel length compared to controls.

FIG. 16 illustrates the significant inhibition of tube formation in the presence of the CatS 1E11 antibody. Photographs of the ring segments are shown in FIG. 16a with the results summarised in FIG. 16b. Incubation of the rat aortic ring segments with up to 600 nM of 1E11 resulted in greater than 80% reduction in total vessel number, mean vessel length and maximum vessel length (FIG. 16b).

FIG. 17 illustrates the significant inhibition of tube formation in a repeat experiment in the presence of the CatS 1E11 antibody. Photographs of the ring segments are shown in FIG. 17a with the results summarised in FIG. 17b. Incubation of the rat aortic ring segments with up to 10 µg/ml of 1E11 resulted in a 70% reduction in total vessel number and a 60% reduction in both mean vessel length and maximum vessel length.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCES

Chapman et al (1997 *Annu Rev Physiol.* 59, 63-88.
Katunuma et al (2003) *Biol. Chem.* 384, 883-90.

Lah T T, Kos J. (1998). *Biol. Chem.* 379: 125-30.
Folkman J, Ingber D. (1992) *Semin Cancer Biol.* 3, 89-96.
Fernandez et al (2001). *Int J Cancer.* 95, 51-5.
Koblinski et al. (2000). *Clin Chim Acta.* 291, 113-35.
Rao J S. (2003). *Nat Rev Cancer.* 3, 489-501.
Kos et al (2001). *Br J Cancer.* 85, 1193-200.
Flannery et al (2003). *Am J Pathol.* 163, 175-82.
Liuzzo et al (1999). *Mol. Med.* 5, 334-43.
Baker et al (2002). *J Virol.* 76, 10905-13.
Lemere et al (1995). *Am J Pathol.* 146, 848-60.
Cheng et al (2006). *Am J Pathol.* 168, 685-94.

The invention claimed is:

1. A pharmaceutical composition comprising a chemotherapeutic agent and a Cathepsin S inhibitor which is a Cathepsin S antibody molecule that does not inhibit proteolytic activity of Cathepsin S, wherein said Cathepsin S antibody molecule is a 1E4 antibody which is the antibody produced from a hybridoma cell line deposited under ECACC Accession No. 15072905.

2. A pharmaceutical kit comprising a Cathepsin S inhibitor which is a Cathepsin S antibody molecule that does not inhibit the proteolytic activity of Cathepsin S and a chemotherapeutic agent for combination therapy by simultaneous, sequential or separate administration of the Cathepsin S inhibitor and chemotherapeutic agent, wherein said Cathepsin S antibody molecule is a 1E4 antibody which is the antibody produced from a hybridoma cell line deposited under ECACC Accession No. 15072905.

3. A pharmaceutical composition comprising an antibody molecule that specifically binds Cathepsin S, but does not inhibit proteolytic activity of Cathepsin S, wherein said antibody molecule that specifically binds Cathepsin S is a 1E4 antibody which is the antibody produced from a hybridoma cell line deposited under ECACC Accession No. 15072905.

4. The pharmaceutical composition according to claim 3, further comprising an anti VEGF antibody.

5. The pharmaceutical composition according to claim 3, further comprising an anti-EGF receptor antibody.

* * * * *

SEQUENCE LISTING

```
<160> NUMBER OF SEQ ID NOS: 12

<210> SEQ ID NO 1
<211> LENGTH: 5
<212> TYPE: PRT
<213> ORGANISM: Mus musculus
<220> FEATURE:
<223> OTHER INFORMATION: CDR amino acid sequence

<400> SEQUENCE: 1

Ser Tyr Asp Met Ser
1               5

<210> SEQ ID NO 2
<211> LENGTH: 17
<212> TYPE: PRT
<213> ORGANISM: Mus musculus
<220> FEATURE:
<223> OTHER INFORMATION: CDR amino acid sequence

<400> SEQUENCE: 2

Tyr Ile Thr Thr Gly Gly Val Asn Thr Tyr Tyr Pro Asp Thr Val Lys
1               5                   10                  15

Gly

<210> SEQ ID NO 3
<211> LENGTH: 6
<212> TYPE: PRT
<213> ORGANISM: Mus musculus
<220> FEATURE:
<223> OTHER INFORMATION: CDR amino acid sequence

<400> SEQUENCE: 3

His Ser Tyr Phe Asp Tyr
1               5

<210> SEQ ID NO 4
<211> LENGTH: 16
<212> TYPE: PRT
<213> ORGANISM: Mus musculus
<220> FEATURE:
<223> OTHER INFORMATION: CDR amino acid sequence

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Mus musculus
<220> FEATURE:
<223> OTHER INFORMATION: CDR amino acid sequence

<400> SEQUENCE: 5

Lys Val Ser Asn Arg Phe Ser
1               5

<210> SEQ ID NO 6
```

```
<211> LENGTH: 9
<212> TYPE: PRT
<213> ORGANISM: Mus musculus
<220> FEATURE:
<223> OTHER INFORMATION: CDR amino acid sequence

<400> SEQUENCE: 6

Ser Gln Thr Thr His Val Pro Pro Thr
1               5

<210> SEQ ID NO 7
<211> LENGTH: 114
<212> TYPE: PRT
<213> ORGANISM: Mus musculus
<220> FEATURE:
<223> OTHER INFORMATION: VH domain amino acid sequence

<400> SEQUENCE: 7

Val Gln Leu Gln Glu Ser Gly Gly Val Leu Val Lys Pro Gly Gly Ser
1               5                   10                  15

Leu Lys Leu Ser Cys Ala Ala Ser Gly Phe Ala Phe Ser Ser Tyr Asp
            20                  25                  30

Met Ser Trp Val Arg Gln Thr Pro Glu Lys Arg Leu Glu Trp Val Ala
        35                  40                  45

Tyr Ile Thr Thr Gly Gly Val Asn Thr Tyr Tyr Pro Asp Thr Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Lys Ser Glu Asp Thr Ala Met Tyr Tyr Cys Ala
                85                  90                  95

Arg His Ser Tyr Phe Asp Tyr Trp Gly Gln Gly Thr Thr Val Thr Val
            100                 105                 110

Ser Ser

<210> SEQ ID NO 8
<211> LENGTH: 113
<212> TYPE: PRT
<213> ORGANISM: Mus musculus
<220> FEATURE:
<223> OTHER INFORMATION: VL domain amino acid sequence

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr His Val Pro Pro Thr Phe Gly Ser Gly Thr Lys Leu Glu Ile Lys
            100                 105                 110

Arg

<210> SEQ ID NO 9
```

```
<211> LENGTH: 22
<212> TYPE: DNA
<213> ORGANISM: Artificial
<220> FEATURE:
<223> OTHER INFORMATION: Sense CatS-specific primer

<400> SEQUENCE: 9
actcagaatg tgaatcatgg tg                                              22

<210> SEQ ID NO 10
<211> LENGTH: 21
<212> TYPE: DNA
<213> ORGANISM: Artificial
<220> FEATURE:
<223> OTHER INFORMATION: Antisense CatS-specific primer

<400> SEQUENCE: 10
ttcttgccat ccgaatatat c                                               21

<210> SEQ ID NO 11
<211> LENGTH: 21
<212> TYPE: DNA
<213> ORGANISM: Artificial
<220> FEATURE:
<223> OTHER INFORMATION: Beta 3 integrin primer

<400> SEQUENCE: 11
cctacatgac cgaaaatacc t                                               21

<210> SEQ ID NO 12
<211> LENGTH: 21
<212> TYPE: DNA
<213> ORGANISM: Artificial
<220> FEATURE:
<223> OTHER INFORMATION: Beta 3 integrin primer

<400> SEQUENCE: 12
aatccctccc cacaaatact g                                               21
```